(12) United States Patent
Johnson

(10) Patent No.: US 7,960,523 B2
(45) Date of Patent: *Jun. 14, 2011

(54) PROCESSES FOR THE PRODUCTION OF AMINOALKYL GLUCOSAMINIDE PHOSPHATE AND DISACCHARIDE IMMUNOEFFECTORS, AND INTERMEDIATES THEREFOR

(75) Inventor: David A. Johnson, Hamilton, MT (US)

(73) Assignee: Corixa Corporation, Seattle, WA (US)

(*) Notice: Subject to any disclaimer, the term of this patent is extended or adjusted under 35 U.S.C. 154(b) by 887 days.

This patent is subject to a terminal disclaimer.

(21) Appl. No.: 11/867,605

(22) Filed: Oct. 4, 2007

(65) Prior Publication Data

US 2008/0033155 A1 Feb. 7, 2008

Related U.S. Application Data

(63) Continuation of application No. 10/897,194, filed on Jul. 21, 2004, now Pat. No. 7,288,640, which is a continuation-in-part of application No. 10/472,991, filed as application No. PCT/US03/21504 on Jul. 8, 2003, now Pat. No. 7,232,900.

(60) Provisional application No. 60/394,487, filed on Jul. 8, 2002.

(51) Int. Cl.
*C08B 37/00* (2006.01)

(52) U.S. Cl. ....... 536/18.7; 536/1.11; 536/4.1; 536/55.3

(58) Field of Classification Search ................ 536/18.7, 536/1.11, 4.1, 55.3
See application file for complete search history.

(56) References Cited

U.S. PATENT DOCUMENTS

| 5,597,573 | A | 1/1997 | Kamireddy et al. |
| 6,013,640 | A | 1/2000 | Elliott et al. |
| 6,355,257 | B1 | 3/2002 | Johnson et al. |
| 6,525,028 | B1 | 2/2003 | Johnson et al. |
| 7,288,640 | B2 * | 10/2007 | Johnson et al. ............ 536/18.7 |

FOREIGN PATENT DOCUMENTS

| EP | 0172581 A2 | 2/1986 |
| WO | WO 02/12258 A1 | 2/2002 |
| WO | WO 2004/005308 A2 | 1/2004 |
| WO | WO 2004/005308 A3 | 1/2004 |

OTHER PUBLICATIONS

Johnson et al, Bioorganic and Medicinal Chemistry Letters, 1999, 9, 2273-78.*
Gross, Hans V.; "Dichlormethyl-methylether als Reagens fur die organische Synthese and Kohlenhydratchemie"; 1978, *Z. Chemie*, vol. 18, No. 6, pp. 201-210.
Jansson, Karl et al; "2-(Trimethylsilyl)ethyl Glycosides. Transformation into Glycopyranosyl Chlorides"; 1990, *J. Org. Chem.*, vol. 55, pp. 3181-3185.
Johnson, David A. et al.; "Synthesis and Biological Evaluation of a New Class of Vaccine Adjuvants: Aminoalkyl Glucosaminide 4-Phosphates (AGPs)"; 1999, *Bioorganic & Medicinal Chemistry Letters*, vol. 9, pp. 2273-2278.
Koeller, Kathryn M. et al.; "Chemoenzymatic Synthesis of Sialyl-Trimeric-Lewis X"; 2000, *Chem. J. Eur.*, vol. 6, No. 7, pp. 1243-1251.
Kovac, Pavol; "Di- and tri-saccharide glycosyl donors for the synthesis of fragments of the O-specific antigen of *Shigella dysenteriae* type 1"; 1993, *Carbohydrate Research*, vol. 245, pp. 219-231.
Lei, Ping-sheng et al.; "Synthesis of the methyl α-glycosides of a di-, tri-, and a tetra-saccharide fragment mimicking the terminus of the O-polysaccharide of *Vibrio cholerae* O:1 serotype Ogawa"; 1996, *Carbohydrate Research*, vol. 281, pp. 47-60.
Norbeck, Daniel W. et al.; "Synthesis of an Isosteric Phosphonate Analogue of Cytidine 5'-Monophospho-3-deoxy-d-*manno*-2-octulosonic Acid"; 1987, *J. Org. Chem.*, vol. 52, pp. 2174-2179.
Pozsgay, Vince et al.; "Synthesis of Kojidextrins and Their Protein Conjugates. Incidence of Steric Mismatch in Oligosaccharide Synthesis"; 1997, *J. Org. Chem.*, vol. 62, pp. 2832-2846.
Warner, Thomas G. et al.; "Synthesis of 2'-(4-Methylumbelliferyl)-α-d-*N*-acetylneuraminic Acid and Detection of Skin Fibroblast Neuraminidase in Normal Humans and in Sialidosis"; 1979, *Biochemistry*, vol. 18, No. 13, pp. 2783-2787.
Jansson, Karl et al.; "2-(Trimethylsilyl)ethyl Glycosides. Transformation into Glycopyranosyl Chlorides"; 1990, *Journal of Organic Chemistry*, vol. 55, pp. 3181-3185.
Koeller, Kathryn M. et al.; "Chemoenzymatic Synthesis of Sialyl-Trimeric-Lewis X"; 2000, *VCH Verlagsgesellschaft*, vol. 6, No. 7, pp. 1243-1251.
Gross, H.; "Dichlormethyl-methylether als Reagens fur die organische Synthese und Kohlenhydratchemie"; 1978, *Z. Chemie*, vol. 18, No. 6, pp. 201-210.

* cited by examiner

*Primary Examiner* — Shaojia Anna Jiang
*Assistant Examiner* — Ganapathy Krishnan
(74) *Attorney, Agent, or Firm* — Kilpatrick Townsend & Stockton LLP

(57) ABSTRACT

This invention relates to processes for production of alkylamino glucosaminide phosphate compounds, and of disaccharide compounds, including various novel intermediates and intermediate processes. In one aspect, glycosyl halides are produced by reaction of an O-silyl glycoside with a dihalomethyl alkyl ether.

8 Claims, No Drawings

PROCESSES FOR THE PRODUCTION OF AMINOALKYL GLUCOSAMINIDE PHOSPHATE AND DISACCHARIDE IMMUNOEFFECTORS, AND INTERMEDIATES THEREFOR

CROSS-REFERENCES TO RELATED APPLICATIONS

This application is a continuation of U.S. application Ser. No. 10/897,194 filed Jul. 21, 2004 now U.S. Pat. No. 7,288,640, which is a continuation-in-part of U.S. application Ser. No. 10/472,991 filed Sep. 25, 2003 now U.S. Pat. No. 7,232,900, which is a United States national stage application of International patent application PCT/US2003/021504 filed Jul. 8, 2003, which in turn claims priority of U.S. provisional application 60/394,487 filed Jul. 8, 2002. Said provisional application is related to U.S. patent application Ser. No. 10/137,730, filed Apr. 30, 2002, which is a continuation-in-part of U.S. patent application Ser. No. 10/043,086, filed Jan. 8, 2002, which is a continuation-in-part of U.S. patent application Ser. No. 09/905,106, filed Jul. 12, 2001, which is a continuation-in-part of U.S. patent application Ser. No. 09/439,839, filed Nov. 12, 1999, now U.S. Pat. No. 6,303,347, which is a continuation-in-part of U.S. patent application Ser. No. 08/853,826, filed May 8, 1997, now U.S. Pat. No. 6,113,918. This application is also related to U.S. patent application Ser. No. 09/074,720 filed May 7, 1998, now U.S. Pat. No. 6,355,257, which is also a continuation-in-part of U.S. application No. 853,826. This application also claims priority of U.S. provisional application 60/438,585 filed Jan. 6, 2003. All of said patents and applications are incorporated herein by reference, in their totalities.

BACKGROUND OF THE INVENTION

This invention relates to processes for the production of aminoalkyl glucosaminide phosphate (AGP) and of disaccharide compounds. Such compounds have been found to be immunoeffectors, adjuvants for vaccines and the like, and in addition, can possess therapeutic and/or prophylactic properties of their own. In addition, this invention relates to processes for the production of glycosyl halides, which can serve as intermediates in the synthesis of AGP compounds, disaccharides, and structurally related molecules. Further, this invention relates to an improved method for synthesizing (R)-3-n-alkanoyltetradecanoic acids, which are intermediates utilized in production of AGPs.

Aminoalkyl glucosaminide phosphates are described in a number of patents, published patent applications, and journal articles. Such compounds in general have five or six acyl groups in the molecular structure, together with an "aglycon" (nitrogen-containing portion), which may be cyclical or acyclical. AGPs having acyclical aglycon groups are disclosed, for instance, in U.S. Pat. Nos. 6,113,918; 6,303,347 and 6,355,257. AGPs having cyclical aglycon groups are disclosed, for instance, in WO 02/012258.

The above-mentioned documents describe the production of the AGP compounds by two alternative processes. In one process a protected 3-O-acyloxyacylated glycosyl halide containing a phosphonate side chain is coupled with an aminoalkanol or aminoalkanethiol of the type described in the patents. The reaction product is then selectively acylated to provide additional acyl groups, as described, and protecting groups are removed. In the second process, both the phosphonate side chain and the fatty acid groups are incorporated after the coupling reaction. Additional process information for producing AGP compounds is contained in Johnson et al., Bioorg. Med. Chem. Lett. 9: 2273 (1999).

Disaccharides that may be produced by the processes described herein include components of the well known immunostimulant monophosphoryl lipid A (contained, for example in MPL® immunostimulant (Corixa Corp.) Other disaccharides that may be produced are disclosed in, for instance, PCT application WO 01/90129 and U.S. Pat. Nos. 6,013,640; 4,987,237; 4,912,094; 4,436,727; and 4,436,728. In U.S. Pat. No. 6,103,640 the disaccharide was prepared by coupling an N-acyloxyacylated or N-protected glycosyl acceptor unit with a protected and/or 3-O-acyloxyacylated glycosyl donor unit. The protecting groups were variously benzyl (Bn) and 2,2,2-trichloroethoxycarbonyl (Troc) groups. The glycosyl acceptor and donor units were constructed separately using a series of substituent protection and deprotection steps, beginning with the known starting materials benzyl- and 2-(trimethylsilyl)ethyl-2-amino-2-deoxy-4,6-O-isopropylidene-β-D-glucopyranoside, respectively.

Glycosyl halides are used in many processes to introduce a glycoside moiety into a molecule, typically as part of a multistep synthesis in the field of saccharide chemistry. They are useful intermediates for incorporating a wide variety of groups, typically by reaction with nucleophiles, especially oxygen, sulfur, and nitrogen nucleophiles. It would be advantageous to provide a process for producing the AGP and disaccharide compounds using a glycosyl halide as a starting material.

Various ways of producing glycosyl halides have been described. Generally, they involve halogenation of an existing glycoside (which may contain typical protecting groups on reactive moieties such as amino or hydroxyl).

In U.S. Pat. No. 6,299,897, for example, an ethyl ester of the glycoside in question (in this instance, N-acetyl neuraminic acid) is reacted with acetyl chloride to produce the corresponding glycosyl chloride. In U.S. Pat. No. 5,843,463, a glycosyl chloride is produced by reacting the glycoside in question (3-O-allyl-5-O-benzyl-1,2-O-methoxybenzylidene-alpha-D-ribofuranose) with trimethylsilyl chloride. The reaction is conducted by mixing the two reactants or by dissolving the glycoside in the trimethylsilyl chloride.

U.S. Pat. No. 4,613,590 discloses a process for preparation of glycosyl chloride by treatment of the glycoside with titanium tetrachloride. In Sugiyama et al., Org. Lett. 2: 2713 (2000), glycosyl chlorides were prepared by reaction of thioglycosides with chlorosulfoniun chloride.

Kovac, Carbohydr. Res. 245: 219 (2993) prepared a glycosyl chloride by reaction of the glycoside with dichloromethyl methyl ether and zinc chloride. Takeo et al., Carbohydr. Res. 245: 81 (1993) produced a glycosyl chloride by reaction with chlorine. Magnusson et al., J. Org. Chem. 55:3181 (1990) produced a glycosyl chloride by reaction of the 2-(trimethylsilyl)ethyl glycoside with 1,1-dichloromethyl methyl ether in the presence of a catalytic amount of zinc chloride.

SUMMARY OF THE INVENTION

This invention relates to a group of related novel processes for the production of aminoalkyl glucosaminide phosphates and of disaccharides, together with intermediate processes and compounds.

In one aspect, the invention comprises processes for the production of aminoalkyl glucosaminide (AGP) compounds.

In a second aspect the invention relates to a process for producing glycosyl halides that comprises reacting a silyl glycoside with a dihalomethyl alkyl ether in the presence of zinc chloride, zinc bromide, boron trifluoride, or a similar Lewis acid. This step also comprises the first of a two-step process for removing an anomeric silyl protecting group from the silyl glycoside by first reacting it to produce a glycosyl halide, which is then reacted it with a silver salt in the presence of water to produce a hemiacetal.

In another aspect this invention comprises a process comprising first producing the glycosyl halide as above, followed by reaction of the glycosyl halide with a monosaccharide in the presence of a silver salt to form a disaccharide.

Another aspect of this invention comprises a process for producing a disaccharide comprising reacting a monosaccharide with a silyl glycoside.

Yet another aspect of this invention comprises a process for silylation of a disaccharide and optionally for subsequently adding a phosphono side chain to the disaccharide.

A still further aspect of this invention comprises a process for producing a triacylated disaccharide from a disaccharide.

Yet another aspect of the invention is a process for removing an acetyl protecting group from a disaccharide.

Yet a further aspect of this invention comprises a process for production of a phosphorylated disaccharide by (a) selectively protecting the 6'-hydroxyl substituent of a disaccharide; and b) adding a phosphono side chain to the disaccharide at the 5'-position.

A still further aspect of this invention comprises a process for simultaneously removing all silyl-based protecting groups from a disaccharide having a plurality of silyl-based protecting groups.

Yet another aspect of this invention comprises a process for producing an AGP compound via a simultaneous or sequential one-pot triple acylation step. This aspect also comprises a novel diamino diol intermediate.

Still another aspect of the invention comprises a process for producing (R)-3-n-alkanoyloxytetradecanoic acids.

Other aspects of this invention include other novel processes and novel intermediates, and/or will be apparent from the description that follows.

DETAILED DESCRIPTION OF THE INVENTION

Definitions

As Used Herein

"Glycoside" refers to a tetrahydropyran ring bearing a substituent at the 1-position (i.e., at one of the carbon atoms adjacent to the oxygen atom in the ring) that is a hydroxy, optionally substituted alkoxy, or trisubstituted silyloxy group. Glycosides may also contain substituents at other positions, typically protected or unprotected hydroxy or amino groups.

"Silyl glycoside" refers to a glycoside wherein the group attached at the 1-position is a trisubstituted silyloxy group such as a trimethylsilyloxy, tert-butyldimethylsilyloxy, or tert-butyldiphenylsilyloxy group. The silyl component of this group has the formula $R_a R_b R_c Si$, wherein $R_a$, $R_b$, and $R_c$ are independently selected from the group consisting of $C_1$-$C_6$ alkyl, $C_3$-$C_6$ cycloalkyl, and optionally substituted phenyl. Preferably one of the $R_a$, $R_b$, and $R_c$ groups is larger than methyl; relatively hindered groups such as t-butyl, phenyl, and isopropyl are preferred. Included among the silyl components are aryldialkylsilyl, diarylalkylsilyl, and triarylsilyl groups. Typical examples include triisopropylsilyl, triphenylsilyl, t-butyldimethysilyl (TBS), and t-butyldiphenylsilyl (TBDPS) groups. The silyl component of the silyl glycoside is most preferably a TBS or TBDPS group.

The silyl glycoside can generally be represented by the formula (II)

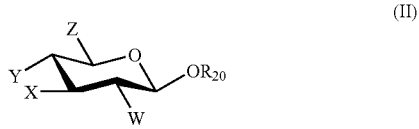

(II)

wherein $R_{20}$ is a trisubstituted silyl group, preferably TBS or TBDPS, and W, X, Y, and Z independently represent H, optionally protected hydroxy, optionally protected amino, or optionally substituted alkyl groups. Typically, Z represents an optionally protected hydroxymethyl group.

"Dihalomethyl alkyl ether" refers to a compound bearing an alkoxy group and two halogen atoms on a single carbon atom. Typical examples include dichloromethyl methyl ether ($CHCl_2OCH_3$), dichloromethyl ethyl ether ($CHCl_2OC_2H_5$), dibromomethyl methyl ether ($CHBr_2OCH_3$), 1,1-dichloroethyl ethyl ether ($CH_3CCl_2OC_2H_5$), and the like. Dichloromethyl methyl ether is preferred in the processes of this invention.

"Glycosyl halide" refers to a 2-halotetrahydropyran compound, for example, 2-chlorotetrahydropyran or 2-bromotetrahydropyran. The preferred halogens are fluoride, chloride, and bromide, with chloride being most preferred. In addition, the glycosyl halides used in the processes of this invention will have other substituents analogous to those in formula (II) above.

Glycosyl halides are generally represented by formula (III):

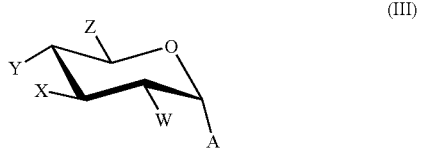

(III)

wherein W, X, Y and Z are as defined above for formula (II) and A is Cl, Br, or F.

"Aliphatic" means a straight or branched chain, or non-aromatic cyclical, hydrocarbon radical, or combination thereof, which may be fully saturated, or mono- or polyunsaturated and can include di- and multivalent radicals, having the number of carbon atoms designated (i.e. $C_1$-$C_{10}$ means one to ten carbon atoms). Examples of saturated acyclic aliphatic groups (also termed "alkyl" groups) include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like. An unsaturated aliphatic group is one having one or more double bonds or triple bonds. Examples of unsaturated acyclic aliphatic groups include, but are not limited to, vinyl, 2-propenyl, isopropenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Examples of cyclical aliphatic groups include cyclopropyl, cyclobutyl, cyclopentyl, cyclohexyl, cyclopentenyl, cyclohexenyl, cyclohexadienyl, and the like.

Divalent aliphatic groups include saturated and unsaturated groups similar to those mentioned above, for example methylene, —$CH_2$—; ethylene, —$CH_2CH_2$—; n-butylene, —CH$_2$CH$_2$CH$_2$CH$_2$—; and unsaturated groups such as —CH═CH—, —CH═CH—CH$_2$CH$_2$— and the like.

The terms "oxyaliphatic", "aminoaliphatic" and "thioaliphatic" are used in their conventional sense, and refer to aliphatic groups attached to the remainder of the molecule via an oxygen atom, an amino group, or a sulfur atom, respectively. "Alkoxy", "thioalkoxy" and "aminoalkyl" refer to such groups containing saturated acyclic aliphatic moieties.

The term "heteroaliphatic," by itself or in combination with another term, means, unless otherwise stated, a group analogous to an aliphatic group, i.e. a saturated or unsaturated straight or branched chain, or cyclic, radical, or combinations thereof, consisting of the stated number of carbon atoms and further comprising at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroaliphatic group or at the position at which that group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$—S(O)—CH$_3$, —CH$_2$—CH$_2$—S(O)$_2$—CH$_3$, —CH═CH—O—CH$_3$, —Si(CH$_3$)$_3$, and —CH$_2$—CH═N—OCH$_3$.

Aliphatic groups may be substituted or unsubstituted. Substituents include a variety of groups selected from: —OR', ═O, ═NR', ═N—OR', —NR'R'', —SR', -halogen, —SiR'R''R''', —OC(O)R', —C(O)R', —CO$_2$R', —CONR'R'', —OC(O)NR'R'', —NR''C(O)R', —NR'—C(O)NR''R''', —NR''C(O)$_2$R', —NR—C(NRR'R'')═NR''', —NR'C(NR'R'')═NR''', —NR—C(NR'R'')═NR''', —S(O)R', —S(O)$_2$R', —S(O)$_2$NR'R'', —NRSO$_2$R', —CN and —NO$_2$ in a number ranging from zero to (2m'+1), where m' is the total number of carbon atoms in such radical. R', R'' and R''' each independently may be hydrogen, optionally substituted alkyl, aryl optionally substituted with 1-3 halogens, optionally substituted alkoxy, optionally substituted thioalkoxy or optionally substituted aryl-(C$_1$-C$_4$)alkyl groups. When a compound of the invention includes more than one R group, for example, each of the R groups is independently selected as are each R', R'' and R''' groups when more than one of these groups is present. When R' and R'' are attached to the same nitrogen atom, they can be combined with the nitrogen atom to form a 5-, 6-, or 7-membered ring. For example, —NR'R'' is meant to include 1-pyrrolidinyl and 4-morpholinyl.

"Aromatic" or "aryl" refers to the typical substituted or unsubstituted non-aliphatic hydrocarbyl groups of this class, i.e., a polyunsaturated, typically aromatic, hydrocarbon substituent, which can be a single ring or multiple rings (up to three rings) which are fused together or linked covalently, such as phenyl, naphthyl, and the like.

"Aralalkyl" refers to alkyl groups subsisted by one or more aryl groups; for instance, benzyl, phenethyl, triphenylmethyl, and the like.

"Acyl" refers to a group derived from an organic acid by removal of the hydroxy group. Acyl compounds may in general be aliphatic, aromatic or heterocyclic in nature. "Aliphatic acyl" refers to such groups derived from saturated or unsaturated aliphatic acids, and includes groups such as acetyl, propionyl, butyryl, hexanoyl, decanoyl, dodecanoyl, tetradecanoyl, and the like. In defining acyl groups by their carbon atom content, the reference is to the carbon atom content of the entire group. Thus, acetyl is a C$_2$ acyl group; propionyl is a C$_3$ acyl group, tetradecanoyl is a C$_{14}$ acyl group, etc.

"Alkanoyloxycarbonyl" refers to groups having a saturated or unsaturated aliphatic group, or an arylalkyl group such as benzyl, linked through an oxygen atom to a carbonyl group, i.e. a group having the general formula Alk.-OC(O)— in which Alk. stands for an aliphatic or arylalkyl group as defined above.

"Alkanoyloxyacyl" refers to a saturated or unsaturated acyl group substituted at the indicated position by an aliphatic group Al.C(O)O— in which Al. stands for an acyclic saturated or unsaturated aliphatic group. The overall alkanoyloxy group preferably has from 2 to 24 carbon atoms, most preferably from 6 to 14 carbon atoms. The acyl portion of the alkanoyloxyacyl group contains from 6 to 14 carbon atoms. A typical group of this type is the 3-(n-alkanoyloxy)acyl group, where the acyl group is tetradecanoyl and the alkanoyloxy group contains from 2 to 20, preferably from 6 to 14, carbon atoms, inclusive. Similarly "alkanoyl" refers to a group Al.C(O)— wherein Al. is as defined above.

"Protecting group" refers to any of a large number of groups used to replace one or both hydrogens of a reactive group such as a hydroxy, amino or thiol group, so as to block, prevent, or reduce reactivity of the group. Examples of protecting groups (and a listing of commonly used abbreviations for them) can be found in T. W. Greene and P. G. Futs, "Protective Groups in Organic Chemistry" (Wiley), Beaucage and Iyer, Tetrahedron 48:2223 (1992) and Harrison et al., Compendium of Synthetic Organic Methods, vols. 1-8 (Wiley).

Representative amino protecting groups include those that form a carbamate or amide with the nitrogen atom, as well as those groups collectively referred to in the Greene and Futs text as "special —NH protective groups". Representative examples of amino protecting groups include acetyl (Ac), trifluoroacetyl, benzyloxycarbonyl (Cbz), tert.-butoxycarbonyl (Boc), allyloxycarbonyl (Aoc), 9-fluorenylmethyloxycarbonyl (Fmoc), nitro-versatryloxycarbonyl (Nvoc), optionally substituted phthaloyl and the like.

Representative hydroxy protecting groups include those where the hydroxy group is either acylated or alkylated, such as by the formation of ethers or esters using, for instance, acetyl, benzyl, trityl, alkyl, tetrahydropyranyl, allyl and trisubstituted silyl groups.

The choice of a protecting group for a given compound, purpose or set of conditions is within the skill of those in the art, and is done so as to protect, generally or selectively, the reactive group in question under the prevailing conditions (presence of other reactive compounds, pH, temperature, etc.) Protecting groups that may be used in this invention and are mentioned herein include phthaloyl, acetyl (Ac), benzyl (Bn), 2,2,2-trichloroethoxycarbonyl (Troc), t-butyldimethylsilyl (TBS or TBDMS), t-butyldiphenylsilyl (TBDPS), and 2,2,2-trichloro-1,1-dimethylethyl chloroformyl (TCBOC) groups. As is known in the art, a certain protecting group or type of group may be more suitable than others for use with a particular compound or in a given situation, and advantage is taken of these suitabilities in developing processes that involve compounds with reactive groups such as hydroxy and/or amino. Thus, as will be seen below, a reaction scheme can be developed for producing or reacting certain compounds in which general or selective protection or deprotection (removal of protecting groups) is carried out at certain points. For instance, in order to selectively react a hydroxy group in a compound that also contains an amino group, or vice versa, the group whose reaction is not desired at this point can be blocked with a protecting group that is not removed under conditions of the reaction (for example, is not base-hydrolyzable if the reaction is to be conducted under basic conditions, while the group to be reacted can be protected by a group that is base-hydrolyzable, so that said group becomes unblocked, and thus reactive, at that time. Similarly as will be seen below, in order to selectively react a group, e.g., a hydroxyl group, located at one position in the molecule, it may be protected with a different protecting group than other hydroxyls in the molecule. As used herein, the designation "PG" refers to protecting groups that form esters, ethers or carbonates with hydroxy groups (i.e., with the oxygen atom of a hydroxy group] or that form amides or carbamates with amino groups [i.e. with the nitrogen atom of an amino group. The designation "PG'" is used herein to refer to optionally substituted phthaloyl groups, for example phthaloyl or tetrachlorophthaloyl, and which may be used to protect an amino group, as shown. However, in any event, the selection of particular protecting groups used or illustrated in the processes described herein is not in any way intended to limit the invention.

The Major Products

The major products produced using the processes and intermediates of this invention comprise a group of compounds that include both AGP compounds, which are monosaccharides, and disaccharides of somewhat analogous structure. In general, the products can be depicted by the formulas (I) and (Ia-c):

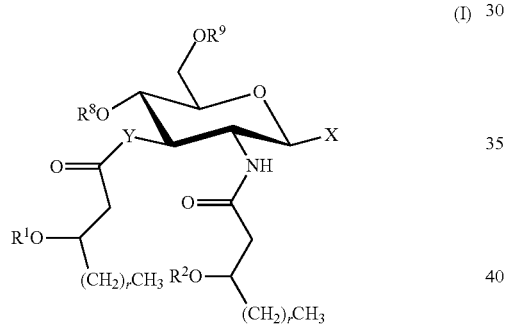

(I)

and pharmaceutically acceptable salts and derivatives thereof, wherein Y is —O— or —NH—; $R^1$ and $R^2$ are each independently selected from saturated and unsaturated ($C_2$-$C_{24}$) aliphatic acyl groups; $R^8$ is —H or —$PO_3R^{11}R^{12}$, wherein $R^{11}$ and $R^{12}$ are each independently —H or ($C_1$-$C_4$) aliphatic groups; $R^9$ is —H, —CH3 or —$PO_3R^{13}R^{14}$, wherein $R^{13}$ and $R^{14}$ are each independently selected from —H and ($C_1$-$C_4$) aliphatic groups; and wherein at least one of $R^8$ and $R^9$ is a phosphorus-containing group, but $R^8$ and $R^9$ are not both phosphorus-containing groups; and X is a group selected from the formulae:

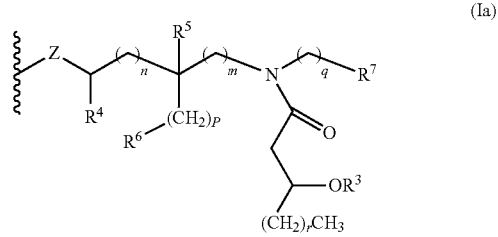

(Ia)

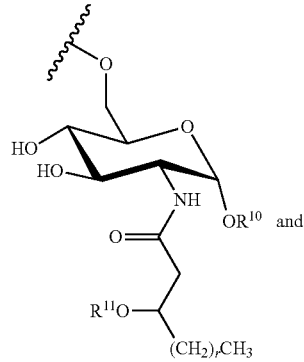

(Ib)

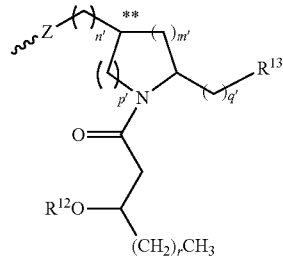

(Ic)

wherein the subscripts n, m, p, q, n', m', p' and q' are each independently an integer of from 0 to 6, provided that the sum of p' and m' is an integer from 0 to 6; the subscript r is independently an integer of from 0 to 14 and may be the same or different; $R^3$, $R^{11}$, and $R^{12}$ are independently saturated or unsaturated aliphatic ($C_2$-$C_{24}$) acyl groups; and when X is formula (Ia) or (Ic) one of $R^1$, $R^2$, $R^3$, $R^{11}$ and $R^{12}$ is optionally hydrogen; $R^4$ and $R^5$ are independently selected from H and methyl; $R^6$ and $R^7$ are independently selected from H, OH, ($C_1$-$C_4$) oxyaliphatic groups, —$PO_3H_2$, —$OPO_3H_2$, —$SO_3H$, —$OSO_3H$, —$NR^{15}R^{16}$, —$SR^{15}$, —CN, —$NO_2$, —CHO, —$CO_2R^{15}$, —$CONR^{15}R^{16}$, —$PO_3R^{15}R^{16}$, —$OPO_3R^{15}R^{16}$, —$SO_3R^{15}$ and —$OSO_3R^{15}$, wherein $R^{15}$ and $R^{16}$ are each independently selected from H and ($C_1$-$C_4$) aliphatic groups; $R^{10}$ is selected from H, $CH_3$, —$PO_3H_2$, ω-phosphonooxy($C_2$-$C_{24}$)alkyl, and ω-carboxy($C_1$-$C_{24}$)alkyl; $R^{13}$ is independently selected from H, OH, ($C_1$-$C_4$) oxyaliphatic groups, —$PO_3R^{17}R^{18}$, —$OPO_3R^{17}R^{18}$, —$SO_3R^{17}$, —$OSO_3R^{17}$, —$NR^{17}R^{18}$, —$SR^{17}$, —CN, —$NO_2$, —CHO, —$CO_2R^{17}$, and —$CONR^{17}R^{18}$, wherein $R^{17}$ and $R^{18}$ are each independently selected from H and ($C_1$-$C_4$) aliphatic groups; and Z is —O— or —S—.

The Processes and Intermediates

One process of this invention comprises the production of glycosyl halides that comprises reacting an O-silyl glycoside with a dihalomethyl alkyl ether in the presence of zinc chloride, zinc bromide, boron trifluoride, or a similar Lewis acid. More specifically, in this process, a glycosyl halide is formed by reacting a silyl glycoside having the formula (II):

(II)

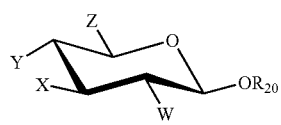

wherein $R_{20}$ is a trisubstituted silyl group having the formula $R_aR_bR_cSi$ in which $R_a$, $R_b$ and $R_c$ are independently selected from the group consisting of $C_1$-$C_6$ alkyl, $C_3$-$C_6$ cycloalkyl and optionally substituted phenyl, preferably TBS or TBDPS, and W, X, Y, and Z independently represent H, optionally protected hydroxy, optionally protected amino, and optionally substituted alkyl groups, with a dihalomethyl alkyl ether, preferably dichloromethyl methyl ether, in the presence of zinc chloride, zinc bromide, boron trifluoride, or a similarly suitable Lewis acid. The Lewis acid is used in about a stoichiometric amount with respect to the silyl glycoside. The reaction to produce the glycosyl halide is conducted at a temperature of from about −30° C. to about 50° C., preferably from about 0° C. to about 30° C., and in the presence of a solvent such as chloroform, dichloromethane, dichloroethane, or similar solvents that are inert to the conditions required for the reaction. The temperature of the reaction is selected to allow the reactants to substantially dissolve and to prevent the dihalomethyl alkyl ether from boiling away. Yields of the desired product glycosyl halide are generally from about 50 to about 95%. Selection of such solvents is within the knowledge of those of ordinary skill in the art. The silyl glycosides are produced conventionally, typically in a protected form, as is known in the art. However, certain silyl glycosides, such as certain triacetylated silyl glycosides and derivatives thereof, may be produced via novel intermediates described below, which form an aspect of the invention.

One of skill in the art will appreciate that the glycosyl halides may exist as isomers if other substituents are present on the glycosyl halide ring. The invention includes production of the separate isomers as well as mixtures of both isomers. Conditions for reactions of many nucleophiles with glycosyl halides are well known to persons of ordinary skill in the art.

The resulting glycosyl halides thus typically have the formula (III)

(III)

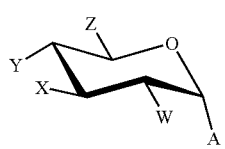

wherein A is Cl, Br, or F and W, X, Y and Z are as defined above.

In one preferred embodiment, the silyl glycoside and resulting products are substituted at the 3-position (substituent X) by an aliphatic acyl group, preferably an alkanoyloxyacyl group, more preferably a 3-n-alkanoyloxyacyl group, and most preferably a 3-alkanoyloxytetradecanoyl group, in which the aliphatic or alkanoyl group contains from 2 to 24, preferably from 2 to 18, and most preferably from 6 to 14, carbon atoms, and the protecting groups in the compound in question are preferably Troc groups or similar alkanoyloxycarbonyl groups. In such embodiments the compounds have the general formula (IV) or (V):

(IV)

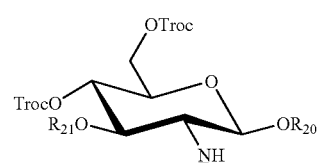

(V)

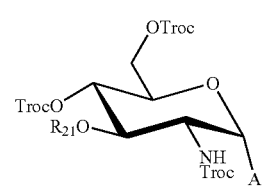

wherein A is Cl, Br, or F; $R_{20}$ is a trisubstituted silyl group and $R_{21}$ is an aliphatic acyl group, preferably a 3-n-alkanoyloxytetradecanoyl group. Note that in this formula and those that follow, protecting groups have been specifically identified for purposes of illustration and/or clarity. However, as known in the art, other protecting groups as defined generally above for "PG" may be used, as suitable. Thus, for instance, more generally these compounds can be represented by the formula (V)

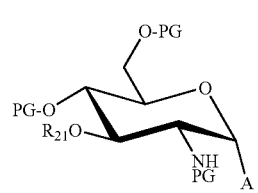

where PG represents protecting groups that form an ether, ester or carbonate with the oxygen atom or that form an amide or carbamate with the nitrogen atom, respectively.

In another preferred embodiment, the silyl glycoside has a hydroxyl group at the 4-position substituted with a phosphate ester group such as a dialkylphosphonyl or diarylphosphonyl group, $R_{21}$ is an alkanoyloxyacyl group, preferably a 3-n-alkanoyloxytetradecanoyl group, and the protecting groups are preferably "TCBOC" groups, obtained from 2,2,2-trichloro-1,1-dimethylethyl chloroformate, or similar alkanoyloxycarbonyl protecting groups such as Troc; i.e., the silyl glycoside may have the specific formula (VI):

(VI)

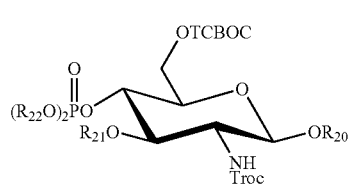

wherein $R_{20}$ is a trisubstituted silyl group, preferably TBS or TBDPS; $R_{21}$ is an aliphatic acyl, preferably an alkanoyloxyacyl, group; and $R_{22}$ is alkyl, aryl, or arylalkyl, or may have a more general formula which allows for the use of other suitable protecting groups, and the glycosyl halide correspondingly has the more specific formula (VII):

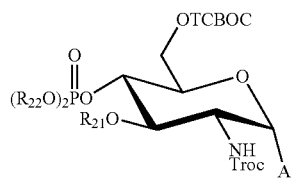
(VII)

wherein $R_{21}$ and $R_{22}$ are as defined above and A is Cl, Br, or F.

In one aspect of the invention the glycosyl chlorides thus produced are reacted with a monosaccharide, preferably in the presence of a silver salt, to produce a disaccharide by this two-step process. Monosaccharides that may be used as reactants in this process include, for example, those having the formulas (i)-(iii):

(i):

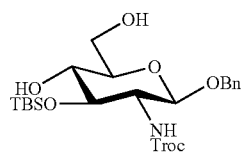

(ii):

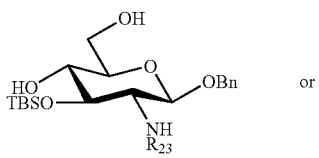

or (iii):

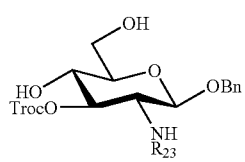

wherein $R_{23}$ is an aliphatic acyl group, preferably a 3-n-alkanoyloxytetradecanoyl group, as described above.

Disaccharides that can be produced by such processes include those having the formulas (iA)-(ivA):

(iA):

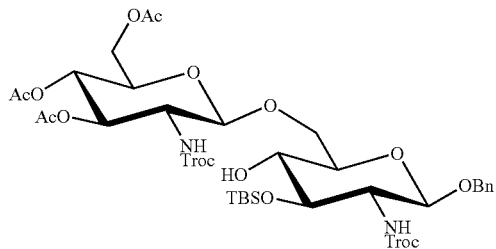

(iiA):

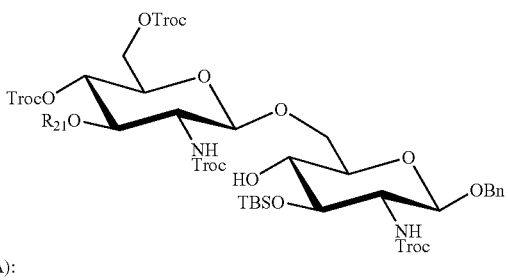

(iiiA):

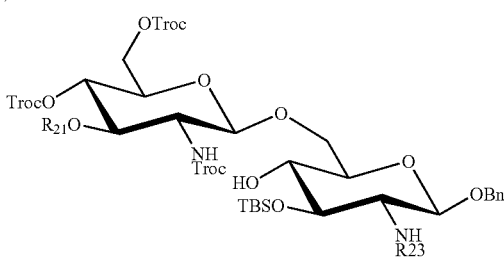

(ivA):

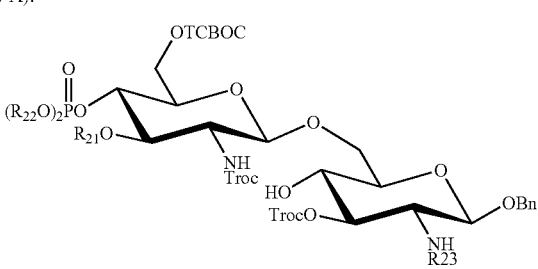

wherein $R_{21}$, $R_{22}$ and $R_{23}$ are as defined above, and the indicated protecting groups are exemplary of those that may be used.

Reactions to produce products (iA)-(ivA) according to this invention are generally conducted at a temperature of from about −30° C. to about 30° C., in a chlorinated or other solvent in the presence of a silver catalyst such as silver trifluoromethanesulfonate (triflate) and under anhydrous conditions, with or without other additives such as molecular sieves or buffering agents such as tetramethylurea.

In another aspect of the invention the silyl glycosides of Formula (II) are coupled with a monosaccharide directly, without proceeding through formation of a glycosyl halide. The resulting product is again a disaccharide having substituents according to the starting materials. Such a process is generally conducted at a temperature of from about −78° C. to about 50° C. in the presence of a suitable Lewis acid catalyst such as trimethylsilyl triflate or boron trifluoride etherate with or without the addition of drying or buffering agents. In another aspect of this invention protecting groups can in effect be removed from a silyl glycoside having such groups by reacting it with a dihaloalkyl ether to produce the glycosyl halide, and then reacting the glycosyl halide with a silver salt such as silver oxide or silver carbonate in the presence of water to produce the corresponding hemiacetal.

The disaccharides produced by either process may be further reacted by silylating the hydroxyl group at the 4-position of the reducing sugar with a silylating group such as TBS in the presence of imidazole and N,N-dimethylformamide to produce a 3,4-bis-silylated compound. Addition of a phosphate group in the 4-position of the non-reducing sugar is then achieved by a sequence of steps involving (1) deprotection of the 4,6 protecting groups (typically acetate or Troc), (2) N-deprotection/acylation, (3) selective protection of the primary 6-position with a group such as TCBOC, and (4) by reacting the 6-protected disaccharide with a phosphonylating agent such as a phosphoramidite reagent, e.g., dibenzyl diisopropylphosphoramidite [providing a dibenzylphosphono side chain], or a chlorophosphate such as bis(2,2,2-trichloroethyl)chlorophosphate [providing a bis(2,2,2-trichloroethyl) phosphono side chain] or diphenyl chlorophosphate [providing a diphenylphosphono side chain].

The invention also, analogously, includes processes for the production of triacylated disaccharides such as those having the formula (VIII):

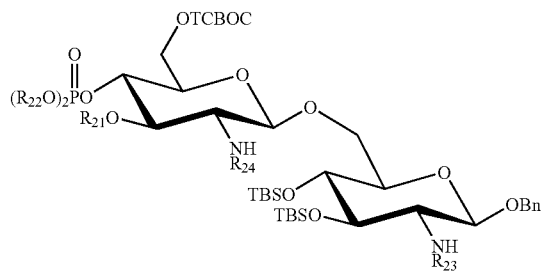

(VIII)

wherein $R_{21}$, $R_{23}$ and $R_{24}$ are aliphatic acyl, preferably alkanoyloxyacyl, groups, and $R_{22}$ is an optionally substituted alkyl, aryl, or arylalkyl group, by selectively protecting the C-6 hydroxyl group of a corresponding disaccharide with 2,2,2-trichloro-1,1-dimethylethyl chloroformate in the presence of a tertiary amine such as pyridine. Preferably, $R_{21}$, $R_{23}$ and $R_{24}$ are (R)-3-hexadecanoyloxytetradecanoyl, (R)-3-octadecanoyloxytetradecanoyl, and (R)-3-tetradecanoyloxytetradecanoyl, respectively, but they can be the same or different depending on the desired substitutions and nature of the monosaccharide donor used in the glycosylation step.

This invention also relates to processes for producing aminoalkyl and cyclic aminoalkyl glucosaminide (AGP) compounds, that is compounds of formula (I) in which X is (Ia) or (Ic), in which both the fatty acid and the phosphate groups are introduced onto the AGP backbone after the initial glycosylation (coupling) step. These processes involve the use of novel glycoside triol intermediates which can be selectively protected in the sugar 6-position prior to the introduction of the ester- and amide-linked acyloxyacyl residues.

One preferred method of the invention for preparing AGP compounds is shown in Scheme 1 below. Scheme 1 depicts the production of specific compounds of Formula (Ia) but is intended to serve only as an example of this aspect of the invention, as the same or a similar process could be used to produce other compounds of the type of Formula (Ia) as well as compounds of Formula (Ic).

In this process introduction of the aliphatic acyl, e.g. (R)-3-n-alkanoyloxy-tetradecanoyl, and phosphate groups into the glucosamine and aglycon units is also performed subsequent to the coupling reaction but, in contrast to the method shown in the prior art patents, the 3-hydroxyl group is selectively esterified with an alkanoic acid substituted by an aliphatic acyl group, preferably an (R)-3-n-alkanoyloxyalkanoic acid, in the presence of an unprotected/ unphosphorylated 4-hydroxyl group with the 6-position blocked. This is achieved by protecting the 6-hydroxyl group of the sugar unit with a persistent protecting group in lieu of temporary protection of the 4,6-hydroxyl positions with an acetonide. Preferably, β-glycoside 8 or the corresponding bis-Troc derivative 9, is de-O-acetylated with a suitable base to give a triol intermediate 10, which is selectively protected on the 6-position with a hindered silyl group such as t-butyldimethylsilyl (TBS) under standard conditions known in the art to give silyl-protected intermediate 12. The triol intermediate 10 is a novel compound. 3-O-Acylation of 12 with (R)-3-n-alkanoyloxytetradecanoic acid, for instance, followed by deprotection/acylation of the sugar and aglycon amino groups, simultaneously (PG=Troc) or sequentially (PG=Aoc), using either zinc (PG=Troc) or zinc and Pd(0) (PG=Aoc) in the deprotection step and (R)-3-n-alkanoyloxytetradecanoic acid in the acylation step, provides hexaacylated intermediate 13. Pentaacylated compounds, i.e. in which one of the acyl groups $R^1$, $R^2$, $R^3$, $R^{11}$ or $R^{12}$ is hydrogen, can be prepared by utilizing different protecting groups for the two amino groups so that one or the other can be selectively acylated; for instance, using an Aoc group for one and a Troc group for the other.

Phosphorylation of the 4-hydroxyl group is carried out by methods known in the art using preferably either a dibenzyl or di-t-butyl protected chlorophosphate or phosphoramidite reagent to give the phosphotriester 14. The phosphate, silyl and any remaining protecting groups in 14 are then cleaved under mildly acidic conditions or by other appropriate means to give compounds of Formula (Ia). It is important to note that the order in which the phosphate and N-linked (R)-3-n-alkanoyloxytetradecanoyl groups in 14 are introduced can be reversed by the appropriate selection of orthogonal phosphate and amine protecting groups.

A variant of the method shown in Scheme 1 is shown in Scheme 2 and involves the incorporation of the three acyl residues, preferably an (R)-3-n-alkanoyloxyalkanoic acid or (R)-3-n-alkyloxyalkanoic acid 4, in a one-pot reaction, either sequentially or simultaneously, onto a diamino diol intermediate 18a. This is achieved by employing a commercially or readily available glycosyl donor such as 15 possessing an N-acetyl, N-phthaloyl (phthalimide, Phth), N-alkoxycarbonyl (carbamate), or other suitable nitrogen protecting group and an anomeric acetoxy, halide group, or other suitable activating group. Again, Scheme 2 is representative of processes of the invention for producing compounds of Formula (Ia) or (Ic).

In Scheme 2, glycosyl donor 15 is coupled with a similarly N-protected acceptor unit 16 in the presence of a catalyst to give β-glycoside 17. As in Scheme 1, a hydroxyl protecting group that is orthogonal to the nitrogen protecting groups is used for protection of the 6-position. For example, when N-acetyl and other N-protecting groups removed under basic conditions are employed, the use of a base-stable ether-type protecting group such as triphenylmethyl (trityl, Tr) on the 6-position is generally required. Alternatively, when carbamate or phthalimide protection of the nitrogen groups is employed, other hydroxyl protecting groups can be used in the 6-position in addition to the trityl group. For example, one preferred embodiment of this invention involves the use of N-carbobenzyloxycarbonyl (Cbz), N-allyloxycarbonyl (Aoc), or N-phthaloyl (Phth) for nitrogen protection and a hindered silyl group such at t-butyldimethylsilyl (TBS) or t-butyldiphenylsilyl (TBDPS) for 6-hydroxyl protection. Although 2,2,2-trichloroethoxycarbonyl (Troc) protection of the nitrogen groups can also be employed as in Scheme 1, Troc deprotection under standard conditions with zinc leads to the formation of complexed zinc which is difficult to remove, leading to low yields of intermediate 18a. Thus, N-protecting groups such as Cbz or Aoc that can be removed under essentially neutral conditions, with or without an intermediate aqueous extraction step, or groups such as N-phthaloyl (phthalimide) or N-acetyl (acetamide) that can be removed in the presence of a resin-bound diamine (phthalimide deprotection) or with an aqueous base such as barium hydroxide that is readily removed by filtration after conversion to an insoluble salt (acetamide deprotection) are preferred. Accordingly, de-O-acetylation of 17 under standard conditions followed by selective protection of the 6-position as a trityl or hindered silyl ether or other suitable hydroxyl protecting group gives diol 18. Removal of the nitrogen protecting groups by appropriate means provides diamino diol intermediate 18a. In one preferred embodiment of this invention, the diamino diol 18a has the following structural formula:

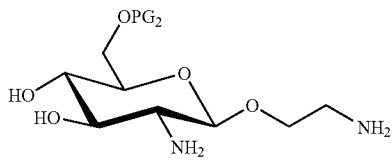

where $PG_2$ is a protecting group as defined above, preferably TBS or trityl.

Simultaneous or sequential N- and O-acylation of 18a with (R)-3-n-alkanoyloxy- or (R)-3-n-alkyloxy-alkanoic acid 4 in the presence of a suitable catalyst affords the hexaacylated derivative 19. Phosphorylation of 19 with a chlorophosphate or phosphoramidite reagent as in Scheme 1 gives phosphate 20. Deprotection of the phosphate, 6-protecting group $PG_2$, and any remaining protecting groups under mildly acidic conditions or by other appropriate means provides compounds of Formula (Ia) or (Ic).

SCHEME 1

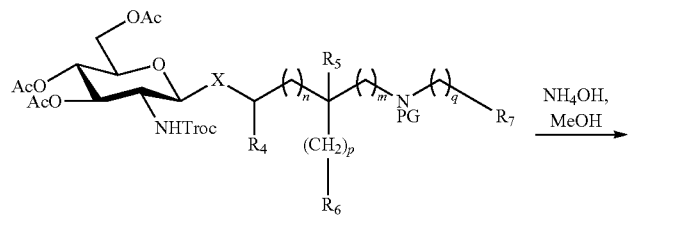

8 PG = Aoc
9 PG = Troc

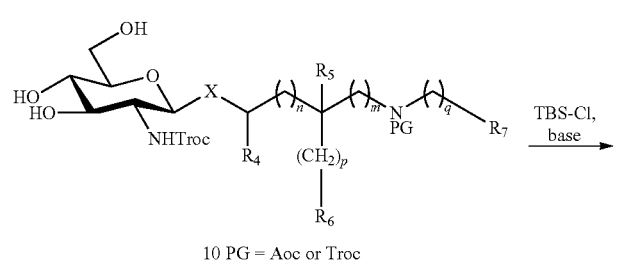

10 PG = Aoc or Troc

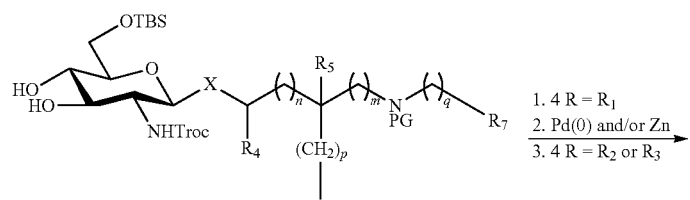

12 PG = Aoc or Troc

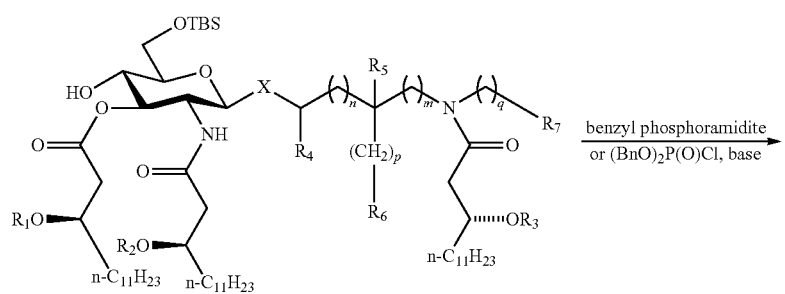

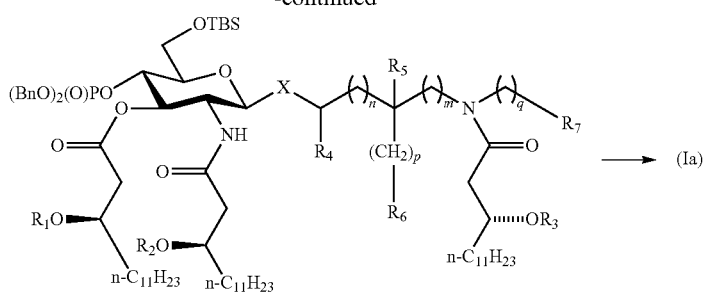
14
SCHEME 2
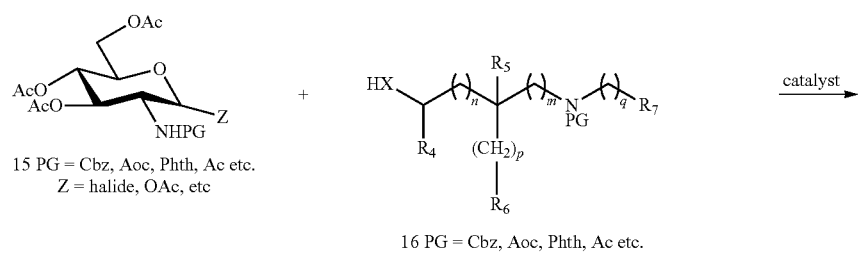
15 PG = Cbz, Aoc, Phth, Ac etc.
Z = halide, OAc, etc
16 PG = Cbz, Aoc, Phth, Ac etc.
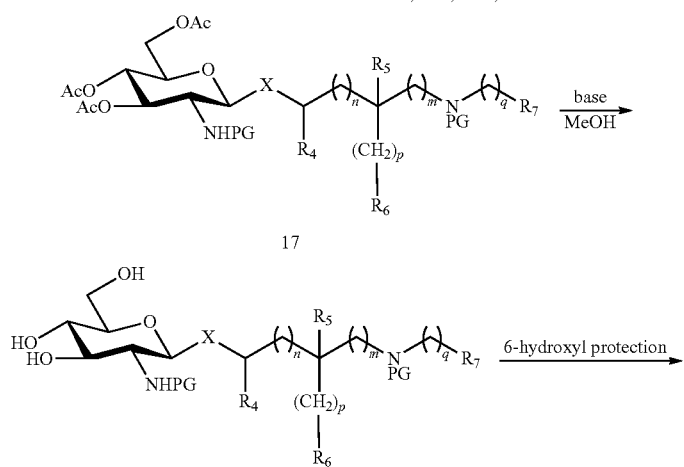
17
17a
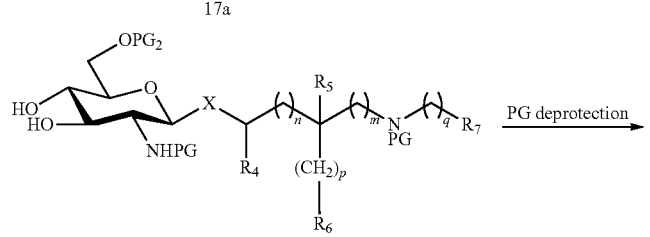
18 PG$_2$ = trityl, silyl, etc.
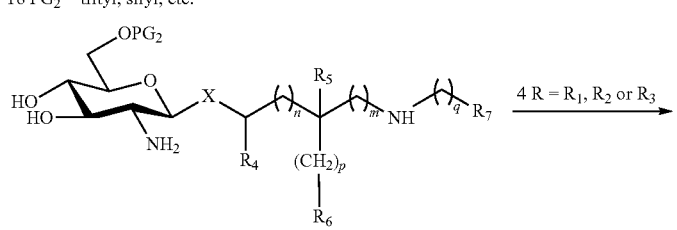
18a

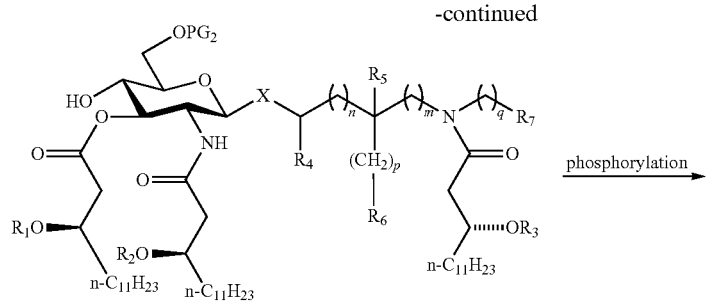

19

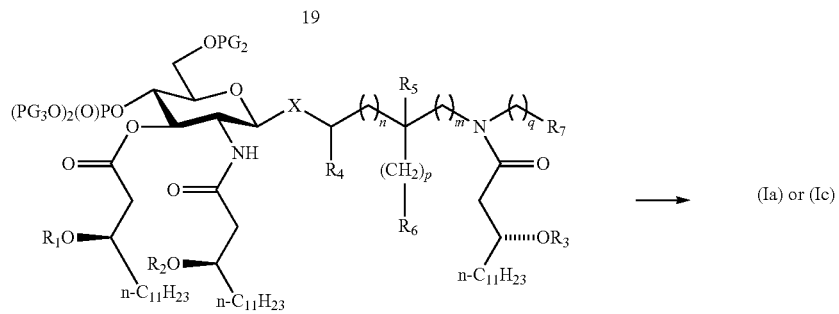

20

In the above Schemes 1 and 2 the various groups $R_1R_7$, n, p and q are as defined above.

Another aspect of the invention comprises a novel method for producing the (R)-3-n-alkanoyloxytetradecanoic acids used in the foregoing processes.

The prior art (for example, U.S. Pat. No. 6,303,347, Example 1) has reported the enantioselective synthesis of (R)-3-alkanoyloxytetradecanoic acids 6 via Ru(II)-Binap-catalyzed hydrogenation of keto ester 3 in the key step using commercially available Noyori-type catalysts and subsequent e.e. enhancement by recrystallization of the dicyclohexylammonium salt of 4. However, reproducibility problems with commercially available catalysts were encountered, as well as difficulties in removing the DCHA-HBr by-product in scale-up preparations of PAc ester 5. There thus is a need for alternate methods for the synthesis of 5 and enhancement of its enantiopurity.

According to an aspect of this invention, an in situ-Ru(II) asymmetric hydrogenation method [Madec et al., *Tetrahedron* 2001, 57:2563] was applied to keto ester 3 using anhydrous RuCl$_3$/(R)-Binap, and gave (R)-3-hydroxytetradecanoic acid (4) in ca. 100% crude yield and 94-99% e.e. (HPLC analysis of 5 using Chiralpack® AS column) on up to a 200-g scale. Direct conversion of crude hydroxy acid 4 to scalemic PAc ester 5 and crystallization of the ester from toluene gave 5 in >99.8% e.e. and 64% overall yield from keto ester 3. Compound 5 was converted to acyloxyacids 6a and 6b by O-acylation and reductive deprotection in 91 and 88% yield, respectively.

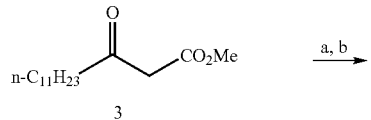

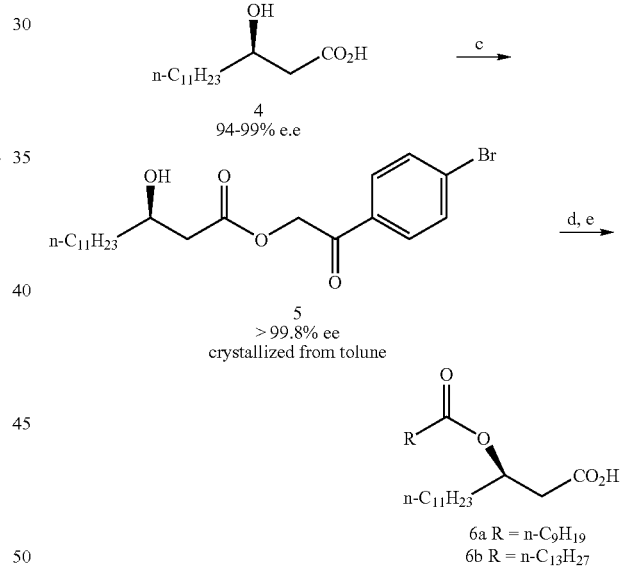

The invention is further illustrated by the examples that follow. These examples are presented solely as illustrative of the invention and do not in any way limit its definition or scope.

Example 1

Production of 2-Deoxy-4-O-diphenylphosphono-3-O—[(R)-3-tetradecanovloxytetradecanoyl]-6-O-(2,2,2-trichloro-1,1-dimethylethoxycarbonyl)-2-(2,2,2-trichloroethoxycarbonylamino)-α-D-glucopyranosyl Chloride This process is depicted in scheme A, below, and includes novel intermediates (iv), (vi) and (vii), which comprise aspects of this invention.

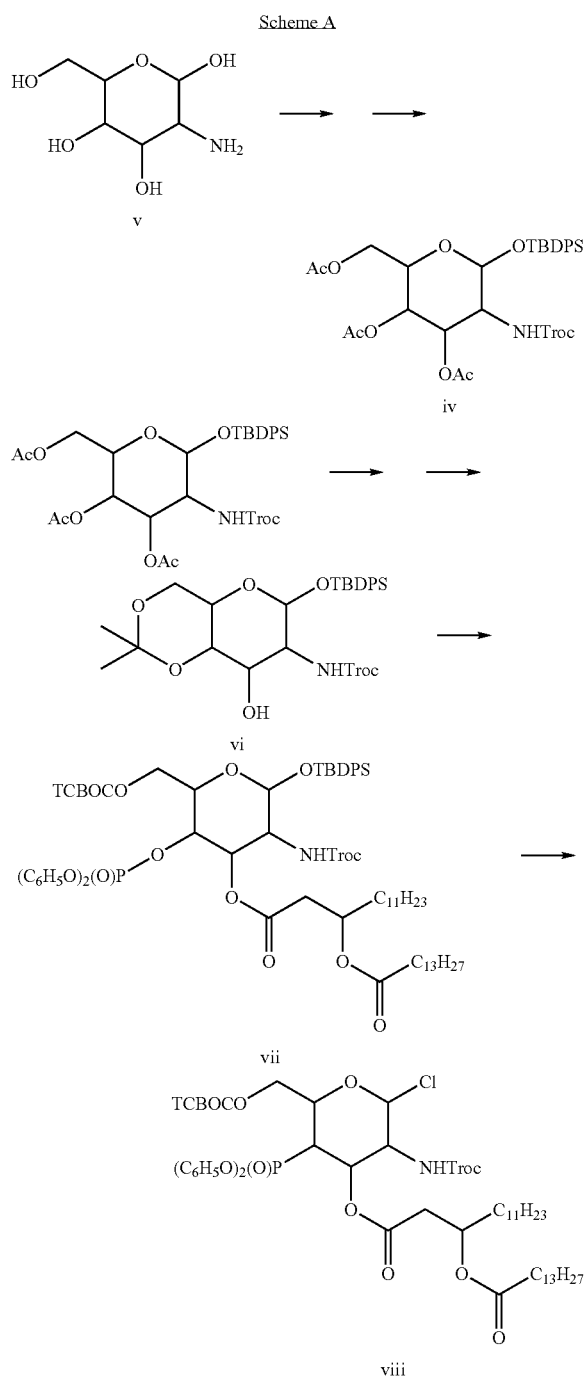

Scheme A (a) Production of t-Butyldiphenylsilyl 2-Deoxy-4,6-O-isopropylidene-2-(2,2,2-trichloroethoxycarbonylamino)-α-D-glucopyranoside (Scheme A, Compound vi)

(1) 2,2,2-Trichloroethoxycarbonyl chloride (200 g, 0.944 mol) is added portionwise to a solution of D-glucosamine hydrochloride (1,200 g, 0.927 mol) and NaHCO$_3$ (200 g, 2.4 mol) in water (4 L) in a 10 L 3-neck round-bottom flask and the resulting mixture is mechanically stirred overnight at room temperature. The white precipitate that forms is collected by filtration using a 2 L flitted funnel, washed with ether (2 L), and dried at high vacuum for 3 hours to give 297 g (90%) of 2-deoxy-2-(2,2,2-trichloroethoxycarbonylamino)-D-glucose as a white solid (MW 354.57).

(2) A solution of 2-deoxy-2-(2,2,2-trichloroethoxycarbonylamino)-D-glucose (297 g, 0.838 mol) obtained in (1) above in a mixture of pyridine (1 L, 12.4 mol) and acetic anhydride (1 L, 10.6 mol) in a 10 L round-bottom flask is mechanically stirred at room temperature overnight. The reaction mixture is concentrated under reduced pressure to give an oil which is azeotroped with toluene (2×1 L) and dried at high vacuum overnight to give 438 g (~100%; 90% from v) of the tetraacetate as a syrup (MW 522.71, TLC (EtOAc) Rf 0.75).

(3) The tetraacetate obtained in (2) above (438 g, 0.838 mol) is dissolved in EtOAc (4 L) and transferred to a 10 L 3-neck round-bottom flask, treated with morpholine (200 mL, 2.29 mol), and mechanically stirred for 8 hours at room temperature. Reaction completion determined by TLC (50% EtOAc/hexanes). 3 N aq HCl (2 L) is added and the resulting mixture is stirred for 30 minutes. The mixture is transferred to a 6 L separatory funnel and the layers are separated. The organic phase is washed with saturated aq NaCl (1 L), dried (Na$_2$SO$_4$), and concentrated to give 373 g (93%, 84% from v) of the 1-O-deprotected derivative (hemiacetal) as a white foam (MW 480.67; TLC (50% EtOAc/hexanes) Rf 0.22).

(4) A solution of hemiacetal obtained in (3) above (373 g, 0.776 mol) and imidazole (132 g, 1.94 mol) in N,N-dimethylformamide (DMF, 430 mL, 1.8 M) is treated with t-butylchlorodiphenylsilane (242 mL, 0.931 mol), and stirred for 48 hours at room temperature. Reaction completion is confirmed by TLC (50% EtOAc/hexanes). The reaction mixture is partitioned between ethyl ether (4 L) and water (1 L) in a 6 L separatory funnel and the layers separated. The ether layer is washed with water (1 L), dried (Na$_2$SO$_4$), and concentrated to give a bronze-colored oil which is crystallized from EtOAc-hexanes (~1:2 v/v) in three crops to provide 474 g (85%, 71% from v) of the t-butyldiphenylsilyl glycoside iv as a white solid (MW 719.08; TLC (50% EtOAc/hexanes) Rf 0.44).

(5) A solution of the silyl glycoside obtained in (4) above (474 g, 0.659 mol) in MeOH (2 L) in a 3 L 3-neck round-bottom flask is treated with ammonium hydroxide (300 mL, 4.5 mol) (some precipitation occurs) and stirred at room temperature overnight, and then treated with a second portion of ammonium hydroxide (50 mL, 0.75 mol) and again stirred overnight. Reaction completion is determined by TLC (EtOAc). The reaction mixture is concentrated and the resulting residue is dissolved in EtOAc (500 mL), placed on a pad of silica gel (1 kg) in a 3 L fritted glass funnel, and eluted with 50% EtOAc-hexanes (5 L) and EtOAc (7 L). The fractions containing the product are concentrated in a 3 L round-bottom flask to give 329 g (84%, 60% from A) of the triol (MW 592.97, TLC (EtOAc) Rf 0.35).

(6) A slurry of the triol obtained in (5) above (329 g, 0.555 mol) in 2,2-dimethoxypropane (1.5 L) in a 3 L round-bottom flask is treated with camphorsulfonic acid (6.4 g, 0.028 mol) and magnetically stirred at room temperature overnight, giving a light yellow solution. Solid NaHCO$_3$ (4.6 g, 0.055 mol) is added and the resulting mixture is stirred for 2 hours at room temperature and then concentrated to dryness. The crude product obtained is dissolved in dichloromethane (1.2 L), divided into two equal portions, and placed on silica gel (1 kg, pre-wetted with 30% EtOAc/hexanes) in two separate 3 L fritted glass funnels, and eluted with 30% EtOAc/hexanes (10 L) and 50% EtOAc/hexanes (8 L). Fractions containing purified product are combined and concentrated to give compound vi as an amorphous solid. The product can be further purified by crystallization from hexanes, if necessary.

| | |
|---|---|
| Molecular Formula: | C$_{28}$H$_{36}$Cl$_3$NO$_7$Si |
| Molecular Weight: | 633.04 |
| Theoretical Yield: | 587 g (based on v) |
| Expected Yield: | 306 g (87%, 52% from v) |
| TLC: | Rf 0.60 (EtOAc) |

(b) Production of t-Butyldiphenylsilyl 2-Deoxy-4-O-diphenylphosphono-3-O—[(R)-3-tetradecanoyloxytetradecanoyl]-6-O-(2,2,2-trichloro-1,1-dimethylethoxycarbonyl)-2-(2,2,2-trichloroethoxycarbonylamino)-α-D-glucopyranoside (Scheme A, Compound vii)

(1) A solution of compound vi (141 g, 0.223 mol) in CH$_2$Cl$_2$ (1 L) in a 2 L round-bottom flask is treated with 3-(R)-tetradecanoyloxy)tetradecanoic acid (101.7 g, 0.224 mol), DCC (55 g, as a melt, 0.267 mol) and 4-pyrrolidinopyridine (3.3 g, 0.022 mol), and stirred at room temperature overnight. Reaction completion is determined by TLC (20% EtOAc/hexanes). The reaction mixture is filtered, concentrated to ca. one-half volume, divided into two equal portions, and placed on silica gel (1 kg, pre-wetted with 2.5% EtOAc/hexanes) in two separate 3 L flitted glass funnels. Gradient elution with 2.5%, 5%, and 10% EtOAc/hexanes (8 L each) and concentration of the fractions containing the product in a 3 L round-bottom flask gives 220 g (92%) of the ester (MW 1069.72, TLC (20% EtOAc/hexanes) Rf 0.53).

(2) The ester obtained in (1) above (218 g, 0.204 mol) is suspended in 90% aq AcOH (1 L) in a 3 L round-bottom flask and stirred (on rotary evaporator) at 70° C. for 2.5 hours, giving a milky solution. Reaction completion is determined by TLC (20% EtOAc/hexanes). The reaction mixture is concentrated and residual AcOH is removed azeotropically with toluene (2×500 mL). The crude product obtained is dissolved in 10% EtOAc/hexanes (400 mL), divided into two equal portions, and placed on silica gel (1 kg) in two separate 3 L fritted glass funnels. Gradient elution with 10% EtOAc/hexanes (10 L) and 15%, 20%, and 30% EtOAc/hexanes (5 L each) and concentration of the fractions containing the product gives 193 g (92%, 85% from vi) of the diol (MW 1029.66, TLC (20% EtOAc) Rf 0.10) containing a small amount (<5% by TLC) of 6-O-acetyl by-product (Rf 0.25). (Note: The 6-acetate by-product is readily separated by radial compression chromatography as the 4-diphenylphosphate derivative in step (3) below.)

(3) A magnetically stirred solution of the diol obtained in (2) above (193 g, 0.187 mol) in CH$_2$Cl$_2$ (1 L) at 0° C. is treated with pyridine (18.2 mL, 0.225 mol) followed by 1,1-dimethyl-2,2,2-trichloroethyl chloroformate (49.5 g, 0.206 mol). Progress of the reaction is monitored by TLC (20% EtOAc/hexanes). Once the reaction is completed by TLC (typically 30-60 minutes, but longer reaction times may be required), triethylamine (55 mL, 0.39 mol), 4-pyrrolidinopyridine (13.9 g, 0.094 mol), and diphenyl chlorophosphate (58.2 mL, 0.281 mol), are added sequentially and the resulting mixture is stirred at room temperature overnight. Reaction completion is determined by TLC (20% EtOAc/hexanes). The reaction mixture is concentrated to dryness and the residue obtained is partitioned between EtOAc (1.5 L) and 1.2 N aq HCl (2 L) in a 6 L separatory funnel and the layers separated. The EtOAc layer is washed with water (2 L), dried (Na$_2$SO$_4$), and concentrated. The residue obtained is dissolved in 10% EtOAc/hexanes (500 mL) and purified by gradient elution on a Biotage 150 Hi system (150 L column) with 10% EtOAc/hexanes (50 L), collecting 950 mL fractions. The fractions containing compound vii are combined and concentrated.

| | |
|---|---|
| Molecular Formula: | C$_{70}$H$_{98}$Cl$_6$NO$_{15}$Psi |
| Molecular Weight: | 1465.30 |
| Theoretical Yield: | 326.8 g (based on vi) |
| Expected Yield: | 211 g (77%, 65% from vi) |
| TLC: | Rf 0.47 (20% EtOAc/hexanes) |

(c) Production of 2-Deoxy-4-O-diphenylphosphono-3-O—[(R)-3-tetradecanoyloxy-tetradecanoyl]-6-O-(2,2,2-trichloro-1,1-dimethylethoxycarbonyl)-2-(2,2,2-trichloroethoxycarbonylamino)-α-D-glucopyranosyl Chloride (Scheme A, Compound viii)

A solution of compound vii (192 g, 0.131 mol) in CHCl$_3$ (2 L) at 0° C. in a 5 L round-bottom flask is treated with α,α-dichloromethyl methyl ether (78 mL, 0.87 mol), followed by ZnCl$_2$ (1.0 M in ether, 100 mL, 0.1 mol) dropwise via an addition funnel. The cold bath is removed and the resulting mixture is stirred at room temperature overnight. Reaction completion is determined by TLC (20% EtOAc/hexanes). The reaction mixture is treated with cold saturated aq NaHCO$_3$ (1 L), stirred for 1 hour, and the layers are separated in a 6 L separatory funnel. The organic layer is dried (MgSO$_4$) and concentrated. The residue obtained is purified on a Biotage 150 Hi system (150 L column) eluting with 10% EtOAc/hexanes (80 L, 950 mL fractions). The fractions containing pure product are combined and concentrated.

| | |
|---|---|
| Molecular Formula: | C$_{54}$H$_{79}$Cl$_7$NO$_{14}$P |
| Molecular Weight: | 1245.36 |
| Theoretical Yield: | 163.2 g |
| Expected Yield: | 141 g (86%) |
| TLC: | Rf 0.42 (20% EtOAc/hexanes) |

Example 2

Preparation of (N—[R)-3-Decanoyloxytetradecanoyl]-O-[2-deoxy-4-O-phosphono-2-[(R)-3-decanoyloxytetradecanoylamino]-3-O—[(R)-3-decanoyloxytetradecanoyl]-β-D-ilucopyranosyl]-L-serine Triethylammonium Salt [a compound of Formula (Ia) in which $R_1=R_2=R_3=n-C_9H_{19}CO$, $Z=Y=O$, $n=m=p=q=0$, $r=10$, $R_4=R_5=R_7=R_9=H$, $R_6=CO_2H$, $R_8=PO_3H_2$)], namely

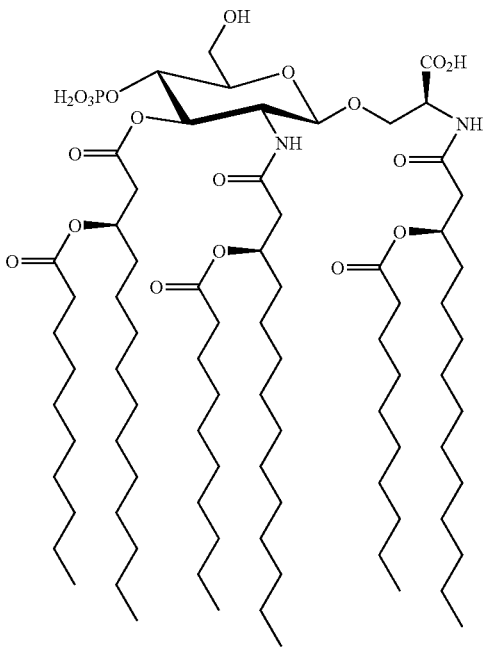

This example utilizes a process as shown in Scheme 1.

(1) A solution of 1,3,4,6-tetra-O-acetyl-2-deoxy-2-(2,2,2-trichloroethoxy-carbonylamino)-β-D-glucopyranoside (5.33 g, 10.2 mmol) and benzyl N-(2,2,2-trichloroethoxycarbonyl)-L-serine (4.16 g, 11.2 mmol) in anhydrous $CH_2Cl_2$ (15 mL) was treated dropwise with boron trifluoride etherate (2.59 mL, 20.4 mmol) and then stirred at room temperature for 2 h. The reaction mixture was quenched with saturated aq. $NaHCO_3$ (20 mL) and the layers separated. The aqueous layer was extracted with $CHCl_3$ (2×10 mL) and the combined organic layers were washed with $H_2O$ (10 mL), dried ($Na_2SO_4$), and concentrated in vacuo. Flash chromatography on silica gel (gradient elution, 20→50% AcOEt/hexanes) afforded 7.42 g (87%) of N-(2,2,2-trichloroethoxycarbonyl)-O-[3,4,6-tetra-O-acetyl-2-deoxy-2-(2,2,2-trichloroethoxycarbonylamino)-β-D-glucopyranosyl]-L-serine benzyl ester as a white solid (compound 9; $X=O$, $n=m=p=q=0$, $r=10$, $R_4=R_5=R_7=H$, $R_6=CO_2Bn$).

(2) A solution of the compound prepared in (1) above (408 mg, 0.49 mmol) in tetrahydrofuran (THF; 20 mL) was hydrogenated in the presence of 10% palladium on carbon (30 mg) at room temperature and atmospheric pressure for 3 h. The reaction mixture was filtered through Celite and the filtrate was concentrated in vacuo. Flash chromatography on silica gel with 2% MeOH—$CHCl_3$ followed by 10% MeOH—$CHCl_3$ afforded 347 mg (98%) of N-(2,2,2-trichloroethoxycarbonyl)-O-[3,4,6-tetra-O-acetyl-2-deoxy-2-(2,2,2-trichloroethoxycarbonylamino)-β-D-glucopyranosyl]-L-serine as a white solid. (compound 9; $X=O$, $n=m=p=q=0$, $r=10$, $R_4=R_5=R_7=H$, $R_6=CO_2H$)

(3) A solution of the compound prepared in (2) above (998 mg, 1.34 mmol) in methanol (15.5 mL) was treated with ammonium hydroxide (0.21 mL, 5.37 mmol) at room temperature for 16 h, followed by additional ammonium hydroxide (0.21 mL, 5.37 mmol) for 24 h. The reaction mixture was concentrated in vacuo and to give a white solid. A suspension of the white solid in $CH_2Cl_2$ (33.5 mL) was treated with benzyl bromide (0.80 mL, 6.7 mmol), tetrabutylammonium bromide (432 mg, 1.34 mmol) and saturated $NaHCO_3$ (33.5 mL) and the resulting biphasic mixture was stirred vigorously at room temperature for 24 h and the layers separated. The aqueous layer was extracted with $CHCl_3$ (2×15 mL) and the combined organic layers were washed with $H_2O$ (10 mL), dried ($Na_2SO_4$), and concentrated in vacuo. The resulting residue was dissolved in anhydrous pyridine (10 mL), treated with t-butyldimethylsilyl chloride (242 mg, 1.61 mmol), and stirred at room temperature for 1.5 h. The reaction mixture was treated with additional t-butyldimethylsilyl chloride (242 mg, 1.61 mmol) and stirred 1.5 h. The reaction mixture was partitioned between $CHCl_3$ (10 mL) and $H_2O$ (10 mL). The aqueous layer was extracted with $CHCl_3$ (2×15 mL) and the combined organic layers were washed with $H_2O$ (15 mL), dried ($Na_2SO_4$) and concentrated in vacuo. Flash chromatography on silica gel using gradient elution (1.0→1.25% $CH_3OH/CHCl_3$) afforded 724 mg (66%) of N-(2,2,2-trichloroethoxycarbonyl)-O-[6-O-t-butyldimethylsilyl-2-deoxy-2-(2,2,2-trichloroethoxycarbonylamino)-β-D-glucopyranosyl]-L-serine benzyl ester as a white solid. (compound 12 PG=Troc, $X=O$, $n=m=p=q=0$, $r=10$, $R_4=R_5=R_7=H$, $R_6=CO_2H$)

(4) A solution of the compound prepared in (3) above (892 mg, 1.09 mmol) in anhydrous $CH_2Cl_2$ (10.5 mL) was treated with (R)-3-decanoyloxytetradecanoic acid (476 mg, 1.20 mmol), 1-(3-dimethylaminopropyl)-3-ethylcarbodiimide methiodide (EDC-MeI; 355 mg, 1.20 mmol), and 4-pyrrolidinopyridine (8 mg, 0.054 mmol) at 0° C. for 1 h. The reaction mixture was treated with additional (R)-3-decanoyloxytetradecanoic acid (60 mg) and EDC.MeI (60 mg) at 0° C., stirred 30 min, and concentrated in vacuo. Flash chromatography on silica gel with 1:6 AcOEt-hexanes afforded 1.10 g (85%) of N-(2,2,2-trichloroethoxy-carbonyl)-O-[6-O-t-butyldimethylsilyl-3-O—[(R)-3-decanoyloxytetradecanoyl]-2-deoxy-2-(2,2,2-trichloroethoxycarbonylamino)-β-D-glucopyranosyl]-L-serine benzyl ester as a colorless oil.

(5) A solution of the compound prepared in (4) above (1.162 g, 0.967 mmol) in 20% aq. THF (16 mL) was treated with zinc dust (632 mg, 9.67 mmol) and acetic acid (0.12 mL, 2.13 mmol) and stirred for 1 h at room temperature. The reaction mixture was filtered through Celite and the filtrate concentrated in vacuo. The resulting off-white solid was dissolved in $CHCl_3$ (15 mL) and washed successively with 15 mL portions of 0.1M HCl, saturated aq $NaHCO_3$, and $H_2O$. The organic layer was dried ($Na_2SO_4$) and concentrated in vacuo and the resulting residue was dried overnight under high vacuum. A solution of the residue in anhydrous $CH_2Cl_2$ (9.5 mL) was treated with (R)-3-decanoyloxytetradecanoic acid (848 mg, 2.13 mmol) and EDC.MeI (632 mg, 2.13 mmol) and stirred at room temperature for 2 h. The reaction mixture was concentrated in vacuo and the residue obtained purified by flash chromatography on silica gel (gradient elution; 20→25% AcOEt/hexanes) to give 1.03 g (66%) of N—[(R)-3-decanoyloxytetradecanoyl]-O-[6-O-t-butyldimethylsilyl-2-deoxy-2-[(R)-3-decanoyloxytetradecanoylamino]-3-O—[(R)-3-decanoyloxytetradecanoyl]-β-D-glucopyranosyl]-L-serine benzyl ester as a glassy solid. (compound 13 $R_1=R_2=R_3=n-C_9H_{19}CO$, $X=O$, $n=m=p=q=0$, $r=10$, $R_4=R_5=R_7=H$, $R_6=CO_2Bn$).

(6) A solution of the compound prepared in (5) above (112 mg, 0.069 mmol) in anhydrous dichloromethane (1 mL) under argon was treated with dibenzyl diisopropyl phosphoramidite (39 μL, 0.12 mmol) and tetrazole (12 mg, 0.173 mmol) and stirred at room temperature for 1 h. The reaction mixture was cooled to 0° C. and treated with m-chloroperbenzoic acid (m-CPBA; 33 mg, 0193 mmol) for 30 min. The reaction mixture was quenched by addition of saturated aq $NaHCO_3$ (5 mL) and stirred at room temperature for 15 min.

The aqueous layer was extracted with chloroform (3×5 mL) and the combined organic layers were washed with water (5 mL), dried (Na$_2$SO$_4$), and concentrated in vacuo. Flash chromatography with 25% AcOEt-hexanes gave partially purified product which was rechromatographed on silica gel with 20% AcOEt-hexanes to give 122 mg (93%) of N—[(R)-3-decanoyloxytetradecanoyl]-O-[6-O-t-butyldimethylsilyl-2-deoxy-4-O-diphenylphosphono-2-[(R)-3-decanoyloxytetradecanoylamino]-3-O—[(R)-3-decanoyloxytetradecanoyl]-β-D-glucopyranosyl]-L-serine benzyl ester as a colorless oil.

(7) A solution of the compound prepared in (6) above (232 mg, 0.124 mmol) in anhydrous THF (10 mL) was hydrogenated in the presence of 20% palladium hydroxide on carbon (46 mg) at room temperature and atmospheric pressure for 36 h. The reaction mixture was filtered through Celite and the filtrate concentrated under vacuum. The resulting oil (181 mg) was dissolved in CH$_2$Cl$_2$ (2.5 mL) and treated with trifluoroacetic acid (29 µL) and stirred under argon at room temperature for 18 h. The reaction mixture was concentrated and co-evaporated with hexanes (2×5 mL). Flash chromatography on silica gel with chloroform-methanol-water-triethylamine (gradient elution; 87:12:0.5:0.5→77:22.5:0.5:0.5) afforded 102 mg (55%) of N—[(R)-3-decanoyloxytetradecanoyl]-O-[2-deoxy-4-O-phosphono-2-[(R)-3-decanoyloxytetradecanoylamino]-3-O—[(R)-3-decanoyloxytetradecanoyl]-β-D-glucopyranosyl]-L-serine triethylammonium salt (RC-527) as a colorless solid.

Example 3

Preparation of (S)-2-[(R)-3-Hexanoyloxytetradecanoylamino]-3-phosphonooxypropyl 2-Deoxy-4-O-phosphono-3-O—[(R)-3-hexanoyloxytetradecanoyl]-2-[(R)-3-hexanoyloxytetradecanoylamino]-β-D-glucopyranoside Bis(triethyl)ammonium Salt [a compound of Formula (I) in which X is (Ia), namely R=R$_2$=R$_3$=n-C$_5$H$_{11}$CO, Z=Y=O, n=m=p=q=0, r=10, R$_4$=R$_5$=R$_7$=R$_9$=H, R$_6$=CH$_2$OPO$_3$H$_2$, R$_8$=PO$_3$H$_2$], namely

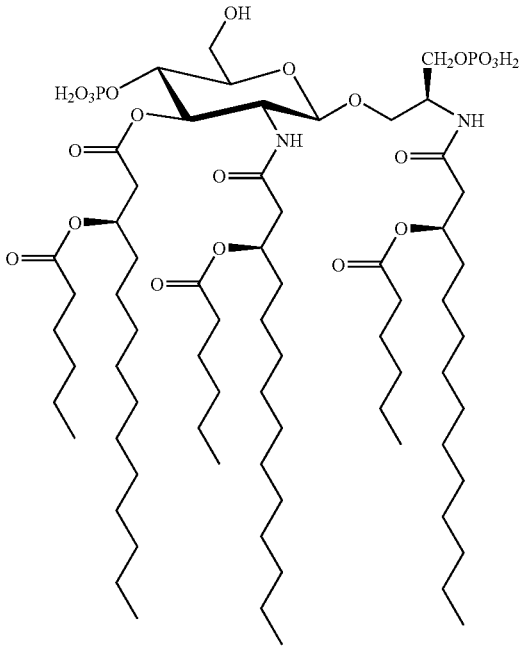

This example utilizes a process as shown in Scheme 1.

(1) In the same manner as described in Example 2-(3), 1,3,4,6-tetra-O-acetyl-2-deoxy-2-(2,2,2-trichloroethoxycarbonylamino)-β-D-glucopyranoside (0.62 g, 1.18 mmol) and (S)-2-(2,2,2-trichloroethoxycarbonylamino)-3-benzyloxy-1-propanol (0.46 g, 1.30 mmol) were coupled in the presence of boron trifluoride etherate (0.3 mL, 2.4 mmol) to give (R)-2-(2,2,2-trichloroethoxycarbonylamino)-3-benzyloxy-1-propyl 2-deoxy-3,4,6-tetra-O-acetyl-2-(2,2,2-trichloroethoxycarbonylamino)-β-D-glucopyranoside as a light yellow solid. (compound 9; X=O, n=m=p=q=0, r=10, R$_4$=R$_5$=R$_7$=H, R=CH$_2$Obn). A solution of this compound in methanol (15 mL) was treated with ammonium hydroxide (0.21 mL, 5.37 mmol) at room temperature for 19 h, followed by additional ammonium hydroxide (0.20 mL, 5.1 mmol) for 25 h. The reaction mixture was concentrated in vacuo and to give a white solid. Flash chromatography on silica gel (gradient elution 5→6% CH$_3$OH/CHCl$_3$) afforded 0.57 g (63%) of 3-benzyloxy-(R)-2-(2,2,2-trichloroethoxycarbonylamino) propyl 2-deoxy-2-(2,2,2-trichloroethoxycarbonylamino)-β-D-glucopyranoside as a glassy solid.

(2) A solution of the compound prepared in (2) above (0.57 g, 0.83 mmol) in anhydrous pyridine (8.5 mL) was treated with t-butyldimethylsilyl chloride (0.15 g, 0.99 mmol) and stirred at room temperature for 1.5 h. Additional t-butyldimethylsilyl chloride (0.15 g, 0.99 mmol) was added and after another 1.5 h the reaction mixture was partitioned between CHCl$_3$ (10 mL) and H$_2$O (10 mL) and the layers separated. The aqueous layer was extracted CHCl$_3$ (2×10 mL) and the combined organic layers were washed with H$_2$O (10 mL), dried (Na$_2$SO$_4$), and concentrated in vacuo. Flash chromatography on silica gel (gradient elution; 80:1→60:1 CHCl$_3$/CH$_3$OH) afforded 0.65 g (98%) of 3-benzyloxy-(R)-2-(2,2,2-trichloroethoxycarbonylamino)propyl 6-O-t-butyldimethylsilyl-2-deoxy-2-(2,2,2-trichloroethoxycarbonylamino)-β-D-glucopyranoside as a white solid.

(3) In the same manner as described in Example 2-(4), the compound prepared in (2) above (0.47 g, 0.59 mmol) was acylated with (R)-3-hexanoyloxytetradecanoic acid (0.22 g, 0.64 mmol) in the presence of EDC-MeI (0.21 g, 0.70 mmol) and 4-pyrrolidinopyridine (4 mg, 0.03 mmol) to afford 0.58 g (88%) of 3-benzyloxy-(R)-2-(2,2,2-trichloroethoxy-carbonylamino)propyl 6-O-t-butyldimethylsilyl-3-O—[(R)-3-hexanoyloxytetradecanoyl]-2-deoxy-2-(2,2,2-trichloroethoxycarbonylamino)-β-D-glucopyranoside as a colorless oil.

(4) In the same manner as described in Example 2-(5), the compound prepared in (3) above (0.58 g, 0.51 mmol) was deprotected with zinc (0.34 g, 5.14 mmol) and acylated with (R)-3-hexanoyloxytetradecanoic acid (0.39 g, 1.13 mmol) in the presence of EDC.MeI (0.34 g, 1.13 mmol) to afford 0.41 g (56%) of 3-benzyloxy-(R)-2-[(R)-3-hexanoyloxy-tetradecanoylamino]propyl 6-O-t-butyldimethylsilyl-3-O—[(R)-3-hexanoyloxytetradecanoyl]-2-deoxy-2-[(R)-3-hexanoyloxytetradecanoylamino]β-D-glucopyranoside as a colorless oil (compound 13 R$_1$=R$_2$=R$_3$=n-C$_5$H$_{11}$CO, X=O, n=m=p=q=0, r=10, R$_4$=R$_5$=R$_7$=H, R$_6$=CH$_2$Obn).

(5) A solution of the compound prepared in (4) above (0.41 g, 0.29 mmol) in THF (18 mL) was hydrogenated in the presence of palladium hydroxide (0.04 g) at room temperature and atmospheric pressure for 17 h. The reaction mixture was filtered through Celite, and the filtrate concentrated in vacuo. Flash chromatography on silica gel (gradient elution; 1:2→1:8 ethyl acetate/heptane) provided 0.3 g (77%) of 3-hydroxy-(R)-2-[(R)-3-hexanoyloxytetradecanoylamino] propyl 6-O-t-butyldimethylsilyl-3-O—[(R)-3-hexanoyloxytetradecanoyl]-2-deoxy-2-[(R)-3-hexanoyloxytetradecanoylamino]-β-D-glucopyranoside as a colorless oil (compound 13 R$_1$=R$_2$=R$_3$=n-C$_5$H$_{11}$CO, X=O, n=m=p=q=0, r=10, R$_4$=R$_5$=R$_7$=H, R$_6$=CH$_2$OH).

(6) In the same manner as described in Example 2-(6), the compound prepared in (5) above (0.30 g, 0.22 mmol) was phosphorylated with dibenzyl diisopropylphosphoramidite (0.25 mL, 0.75 mmol), tetrazole (0.08 g, 1.11 mmol), and m-CPBA (0.33 g, 1.95 mmol) to give 0.30 g (73%) of 3-dibenzylphosphonooxy-(R)-2-[(R)-3-hexanoyloxy-tetradecanoylamino]propyl 4-dibenzylphosphono-6-O-t-butyldimethylsilyl-3-O—[(R)-3-hexanoyloxytetradecanoyl]-2-deoxy-2-[(R)-3-hexanoyloxytetradecanoylamino]-β-D-glucopyranoside as a colorless oil.

(7) A solution of the compound prepared in (6) above (302 mg, 0.16 mmol) in anhydrous THF (13 mL) was hydrogenated in the presence of 20% palladium hydroxide on carbon (60 mg) at room temperature and atmospheric pressure for 27 h. The reaction mixture was filtered through Celite and the filtrate concentrated in vacuo. A solution of the resulting oil (226 mg) in $CH_2Cl_2$ (3.5 mL) was treated with trifluoroacetic acid (0.04 mL, 0.49 mmol) and stirred under argon at room temperature for 16 h. The reaction mixture was concentrated and co-evaporated with hexanes (2×5 mL), and the resulting residue dried under high vacuum to give crude product (226 mg). A portion of the crude product (102 mg) was dissolved in 1:2 $CHCl_3/CH_3OH$ (9 mL), loaded onto a DEAE-cellulose column (15 g, fast flow, Sigma), and eluted with 2:3:1 $CHCl_3$: $CH_3OH$:$H_2O$ using a 0 to 0.1 M $NH_4Oac$ salt gradient. The fractions containing purified product were combined, washed with 0.1 N aq HCl, and concentrated in vacuo. The residue obtained was lyophilized from 1% aq triethylamine (pyrogen free) to give 82 mg (81%) (S)-2-[(R)-3-hexanoyloxytetradecanoylamino]-3-phosphonooxypropyl 2-deoxy-4-O-phosphono-3-O—[(R)-3-hexanoyloxytetradecanoyl]-2-[(R)-3-hexanoyloxytetradecanoylamino]-β-D-glucopyranoside bis(triethyl)ammonium salt as a white powder: positive FAB-MS calcd for $[M+Na]^+$ 1407.8534, found 1407.8689; $^1$H NMR ($CDCl_3/CD_3OD$): δ (ppm) 5.23-5.16 (m, 4H), 4.67 (d, 1H), 4.38 (dd, 1H), 4.19-3.83 (m, 7H), 3.49 (m, 2H), 3.06 (m, 12H), 2.64-2.23 (m, 12H), 1.58-1.56 (m, 12H), 1.23 (m, 94H), 0.88-0.87 (m, 18H). $^{13}$C NMR ($CDCl_3/CD_3OD$): δ (ppm) 173.7, 173.3, 173.2, 170.3, 170.1, 100.0, 74.6, 74.0, 70.9, 70.8, 70.3, 66.6, 63.5, 60.4, 54.2, 45.8, 41.1, 40.7, 39.3, 34.4, 34.3, 31.9, 31.3, 29.7, 29.4, 25.3, 24.7, 22.7, 22.3, 14.1, 13.9, 8.5.

Example 4

Preparation of 2-[(R)-3-decanoyloxytetradecanoylamino]ethyl 4-O-phosphono-3-O—[(R)-3-decanoyloxytetradecanoyl]-2-deoxy-2-[(R)-3-decanoyloxytetradecanoylamino]-β-D-glucopyranoside triethylammonium Salt [a Compound of Formula (Ia) in which $R_1=R_2=R_3=n-C_9H_{19}CO$, Z=Y=O, n=m=p=q=0, r=10, $R_4$=—$R_6=R_7=R_9$=H, $R_8$—$PO_3H_2$)], Namely

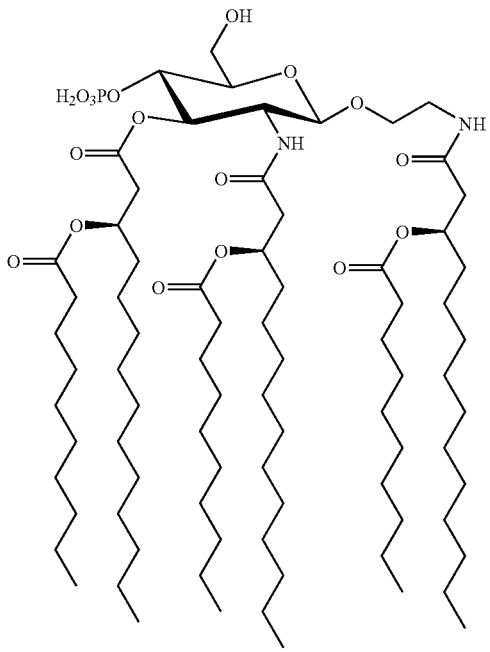

This example utilizes a process as shown in Scheme 2.

(1) 1,3,4,6-Tetra-O-acetyl-2-deoxy-2-(benzyloxycarbonylamino)-β-D-glucopyranoside (compound 15, PG=Cbz, Z=Oac; 19.2 g, 39.9 mmol) and benzyl N-(2-hydroxyethyl) carbamate (8.6 gm, 44 mmol) were dissolved in anhydrous $CH_2Cl_2$ (160 mL, 0.25M), and cooled to −15° C. Trimethylsilyl triflate (0.1 equiv) was added dropwise and the reaction mixture was allowed to warm to room temperature over 5.5 h. The reaction was quenched into saturated $NaHCO_3$ and the layers separated. The aqueous phase was extracted with $CH_2Cl_2$ and the combined organic layers were dried ($Na_2SO_4$), and concentrated. The crude product obtained was crystallized from $CH_2Cl_2$/heptane to give 19.9 gm (81%) of 2-(benzyloxycarbonylamino)ethyl 3,4,6-tri-O-acetyl-2-deoxy-2-(benzyloxycarbonylamino)-β-D-glucopyranoside as a white solid (compound 17; X=O, n=m=p=q=0, $R_4=R_5=R_6=R_7$=H, PG=Cbz): mp 129-130° C.

(2) A solution of the compound prepared in (1) above (13.6 g, 22.1 mmol) in methanol (220 mL, 0.1M) was treated with conc. Ammonium hydroxide (20 equiv) and stirred for 2 h at room temperature. The reaction mixture was concentrated and dried under high vacuum overnight to give 11 g (100%) of 2-(benzyloxycarbonylamino)ethyl 2-deoxy-2-(N-benzyloxycarbonylamino)-β-D-glucopyranoside as a white solid (compound 17a; X=O, n=m=p=q=0, $R_4=R_5=R_6=R_7$=H, PG=Cbz), which was used without further purification in the next step.

(3) A solution of the compound prepared in (2) above (8.4 g, 17.2 mmol) in anhydrous pyridine (14 mL, 0.17 mol) at room temperature was treated with TBDMS-Cl (3.1 g, 20.6 mmol) and stirred at room temperature for 2 h. The reaction mixture was diluted with water and extracted with EtOAc. The layers were separated and the organic phase was washed with brine, dried ($Na_2SO_4$), and concentrated. The resulting oil was crystallized from EtOAc/heptane to give 8.8 gm (85%) of 2-(benzyloxycarbonylamino)ethyl 6-O-t-butyldimethylsilyl-2-deoxy-2-(benzyloxycarbonylamino)-β-D-glucopyranoside compound as a white solid (compound 18; X=O, n=m=p=q=0, $R_4=R_5=R_6=R_7$=H, PG=Cbz, $PG_2$=TBDMS): mp 113-115° C.

(4) A solution of the compound prepared in (3) above (1.15 g, 1.90 mmol) in anhydrous methanol (20 mL) was hydrogenated the presence of 5% Pd/C (10% w/w, 115 mg) at room temperature and atmospheric for 24 h. The reaction mixture was filtered through a pad of Celite and the pad rinsed with 2:1 $CHCl_3$-MeOH (2×10 mL). The filtrate was concentrated and dried overnight under high vacuum to give 0.64 g (100%) of 2-aminoethyl 6-O-t-butyldimethylsilyl-2-deoxy-2-amino)-β-D-glucopyranoside as a white solid (compound 18a; X=O, n=m=p=q=0, $R_4=R_5=R_6=R_7$=H, $PG_2$=TBDMS), which was used without further purification in the next step.

(5) A suspension of the compound prepared in (4) above (0.64 g, 1.90 mmol) in anhydrous $CH_2Cl_2$ (20 mL) was treated with (R)-3-decanoyloxytetradecanoic acid (1.67 g, 4.19 mmol) and EDC-MeI (1.24 g, 4.19 mmol) and stirred for 3 h at room temperature. The nearly homogeneous reaction mixture was cooled to 0° C. and treated sequentially with (R)-3-decanoyloxytetradecanoic acid (0.83 g, 2.09 mmol), EDC.MeI (0.62 g, 2.09 mmol) and 4-pyrrolidinopyridine (14 mg, 0.09 mmol) and then stirred at 0° C. under nitrogen for 24 h. The reaction mixture was partitioned between CHCl$_3$ (20 mL) and H$_2$O (30 mL), and the layers were separated. The aqueous layer was extracted with CHCl$_3$ (10 mL) and the combined organic layers were dried (Na$_2$SO$_4$) and concentrated. The residue obtained was purified by flash chromatography on silica gel using EtOAc-heptane (gradient elution; 1:3.5-1:3) to give 1.25 g (44%) of 2-[(R)-3-decanoyloxytetradecanoylamino]ethyl 6-O-t-butyldimethylsilyl-3-O—[(R)-3-decanoyloxytetradecanoyl]-2-deoxy-2-[(R)-3-decanoyloxytetradecanoylamino]-β-D-glucopyranoside as an amorphous solid (compound 19, PG$_2$=TBDMS, Scheme 2; R$_1$=R$_2$=R$_3$=n-C$_9$H$_{19}$CO, X=O, n=m=p=q=0, R$_4$=R$_5$=R$_6$=R$_7$=H).

(6) A solution of the compound prepared in (5) above (1.18 g, 0.80 mmol) in anhydrous CH$_2$Cl$_2$ (10.8 mL) under nitrogen was treated with dibenzyl diisopropyl phosphoramidite (0.46 mL, 1.36 mmol) and 4,5-dicyanoimidazole (DCI; 236 mg, 2.00 mmol) and stirred for 1 h at room temperature. The reaction mixture was then cooled to 0° C., treated with m-CPBA (387 mg, 2.24 mmol) and stirred for 30 min. The reaction mixture was quenched by addition of saturated NaHCO$_3$ (30 mL) and stirred for 15 min at room temperature. The aqueous layer was extracted with chloroform (2×10 mL) and the combined organic layers were washed with brine (20 mL), dried (Na$_2$SO$_4$), and concentrated. The resulting residue was dissolved in anhydrous dichloromethane (17 mL) under nitrogen, treated slowly with trifluoroacetic acid (TFA; 0.62 mL, 8.01 mmol), and then stirred for 1.5 h at room temperature. The reaction mixture concentrated, co-evaporated with heptane (2×10 mL), and dried under high vacuum. Flash chromatography on silica gel with EtOAc-heptane (gradient elution; 1:2→2:1) afforded 0.85 g (65%) of 2-[(R)-3-decanoyloxytetradecanoylamino]ethyl 4-O-dibenzylphosphono-3-O—[(R)-3-decanoyloxytetradecanoyl]-2-deoxy-2-[(R)-3-decanoyloxytetradecanoylamino]β-D-glucopyranoside as an amorphous solid compound 20, PG$_2$=TBDMS, PG$_3$=Bn, Scheme 2; R$_1$=R$_2$=R$_3$=n-C$_9$H$_{19}$CO, X=O, n=m=p=q=0, R$_4$=R$_5$=R$_6$=R$_7$=H).

(7) A solution of the compound prepared in (6) above (0.80 g, 0.49 mmol) in anhydrous THF (28 mL) was hydrogenated in the presence of 20% Pd(OH)$_2$ on carbon (20% w/w, 159 mg) at room temperature and atmospheric pressure for 6 h. The reaction mixture was filtered through a pad of Celite and the pad rinsed with 2:1 CHCl$_3$-MeOH (2×10 mL). The filtrate was concentrated and dried overnight under high vacuum. The resulting residue was suspended in 2% aq triethylamine (TEA, 20 mL), bath sonicated for a few minutes, and lyophilized. Flash chromatography on silica gel with chloroform-methanol-water-triethylamine (gradient elution; 90:10:0.5:0.5-85:15:0.5:0.5) afforded 539 mg (72%) of 2-[(R)-3-decanoyloxytetradecanoylamino]ethyl 4-O-phosphono-3- O—[(R)-3-decanoyloxytetradecanoyl]-2-deoxy-2-[(R)-3-decanoyloxytetradecanoylamino]-β-D-glucopyranoside (RC-524) as a colorless solid.

Example 5

Preparation of 2-[(R)-3-tetradecanovioxytetradecanoylamino]ethyl 4-O-phosphono-3-O—[(R)-3-tetradecanoyloxytetradecanoyl]-2-deoxy-2-[(R)-3-tetradecanovloxytetradecanoylamino]-β-D-glucopyranoside triethylammonium Salt [a Compound of Formula (Ia) in Which R$_1$=R$_2$=R$_3$=n-C$_{13}$H$_{27}$CO, Z=Y=O, n=m=p=q=0, r=10, R$_4$=R$_5$=R$_6$=R$_7$=R$_9$=H, R$_8$=PO$_3$H$_2$)], Namely

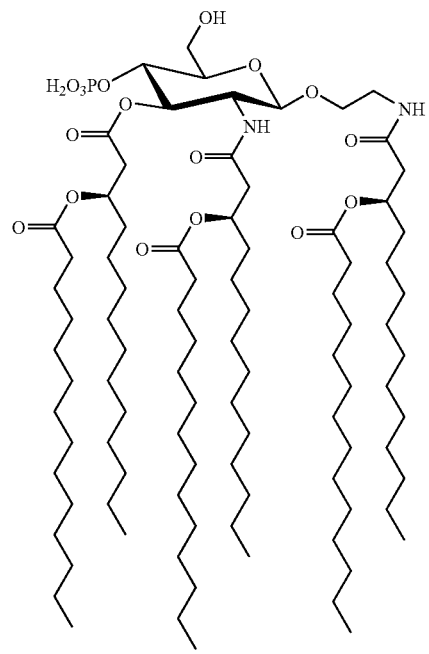

This example utilizes a process as shown in Scheme 2.

(1) In the same manner as described in Example 4-(4), the compound prepared in Example 4-(3) (0.90 g, 1.49 mmol) was hydrogenated in the presence of 5% palladium on carbon (90 mg) in methanol (19 mL) to give 0.50 g (100%) of 2-aminoethyl 6-O-t-butyldimethylsilyl-2-deoxy-2-amino)-β-D-glucopyranoside as a white solid (compound 18a; X=O, n=m=p=q=0, R$_4$=R$_5$=R$_6$=R$_7$=H, PG$_2$=TBDMS) which was used without further purification in the next step.

(2) In the same manner as described in Example 4-(5), the compound prepared in (1) above (0.50 g, 1.49 mmol) in anhydrous CH$_2$Cl$_2$ (15 mL) was acylated with (R)-tetradecanoyloxytetradecanoic acid (2.24 g, 4.93 mmol) in the presence of EDC-MeI and 4-pyrrolidinopyridine to give 1.09 g (44%) of 2-[(R)-3-tetradecanoyloxytetradecanoylamino]ethyl 6-O-t-butyldimethylsilyl-3-O—[(R)-3-tetradecanoyloxytetradecanoyl]-2-deoxy-2-[(R)-3-tetradecanoyloxytetradecanoylamino]-D-glucopyranoside as an amorphous solid (compound 19, PG$_2$=TBDMS, Scheme 2; R$_1$=R$_2$=R$_3$=n-C$_{13}$H$_{27}$CO, X=O, n=m=p=q=0, R$_4$=R$_5$=R$_6$=R$_7$=H).

(3) In the same manner as described in Example 4-(6), the compound prepared in (2) above (1.04 g, 0.63 mmol) was phosphorylated with dibenzyl diisopropyl phosphoramidite (0.36 mL, 1.08 mmol), 4,5-dicyanoimidazole (DCI; 187 mg, 1.58 mmol), and m-CPBA (306 mg, 1.77 mmol) and deprotected with TFA (0.49 mL, 6.33 mmol) to give 1.08 g (95%) of 2-[(R)-3-tetradecanoyloxytetradecanoylamino]ethyl 4-O-dibenzylphosphono-3-O—[(R)-3-tetradecanoyloxytetradecanoyl]-2-deoxy-2-[(R)-3-tetradecanoyloxytetradecanoylamino]β-D-glucopyranoside as an amorphous solid. (compound 20, $PG_2$=TBDMS, $PG_3$=Bn, Scheme 2; $R_1$=$R_2$=$R_3$=n-$C_{13}H_{27}$CO, X=O, n=m=p=q=0, $R_4$=$R_5$=$R_6$=$R_7$=H).

(4) In the same manner as described in Example 4-(7), the compound prepared in (3) above (1.04 g, 0.58 mmol) in anhydrous THF (33 mL) was hydrogenated in the presence of 20% palladium hydroxide (208 mg) to give 296 mg (53%) of 2-[(R)-3-tetradecanoyloxytetradecanoylamino]ethyl 4-O-phosphono-3-O—[(R)-3-tetradecanoyloxytetradecanoyl]-2-deoxy-2-[(R)-3-tetradecanoyloxytetradecanoylamino]β-D-glucopyranoside (RC-529) as a colorless solid.

Example 6

Alternate preparation of 2-aminoethyl 6-O-t-butyldimethylsilyl-2-deoxy-2-amino)-β-D-glucopyranoside (Compound 18a; X=O, n=m=p=q=0, $R_4$=$R_5$=$R_6$=$R_7$=H, $PG_2$-TBDMS), Namely

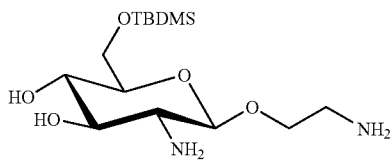

using allyl carbamate (Aoc) protection. This example utilizes a process as shown in Scheme 2.

(1) In the same manner as described in Example 2-(1), allyl N-(hydroxyethyl)carbamate (2.0 g, 14.0 mmol) was glycosylated with 1,3,4,6-tetra-O-acetyl-2-deoxy-2-(allyloxycarbonylamino)-β-D-glucopyranoside (compound 15, PG=Aoc, Z=Oac; 5.19 g, 12.0 mmol) in the presence of $BF_3$-$Oet_2$ (2 equiv) in $CH_2Cl_2$ to give 4.87 g (79%) of 2-(allyloxycarbonylamino)ethyl 3,4,6-tri-O-acetyl-2-deoxy-2-(allyloxycarbonylamino)-β-D-glucopyranoside as a white solid (compound 17; X=O, n=m=p=q=0, $R_4$=$R_5$=$R_6$=$R_7$=H, PG=Aoc).

(2) In the same manner as described in Example 4-(2), the compound prepared in (1) above (4.87 g, 9.43 mmol), was de-acylated with conc $NH_4OH$ (4 equiv) in MeOH to give 3.7 g (100%) of 2-(allyloxycarbonylamino)ethyl 2-deoxy-2-(allyloxycarbonylamino)-β-D-glucopyranoside as a white solid (compound 17a; X=O, n=m=p=q=0, $R_4$=$R_5$=$R_6$=$R_7$=H, PG=Aoc), which was used without further purification in the next step.

(3) In the same manner as described in Example 4-(3), the compound prepared in (2) above (1.27 g, 3.25 mmol) was silylated with TBDMS-Cl (0.91 g, 6.05 mmol) in anhydrous pyridine (32 mL) to give 1.52 g (92%) of 2-(allyloxycarbonylamino)ethyl 6-O-t-butyldimethylsilyl-2-deoxy-2-(allyloxycarbonylamino)-β-D-glucopyranoside compound as a white solid (compound 18; X=O, n=m=p=q=0, $R_4$=$R_5$=$R_6$=$R_7$=H, PG=Aoc, $PG_2$=TBDMS).

(4) A solution of the compound prepared in (3) above (0.77 g, 1.53 mmol) in a mixture of $CH_2Cl_2$ (30 mL) and water (0.15 mL) was treated with $Bu_3SnH$ (2.1 equiv) and $(Ph_3P)_3Pd$ (0.01 equiv) and stirred for 20 min and room temperature. The reaction mixture was concentrated and dried under high vacuum. The resulting yellow solid was triturated with t-butyl methyl ether to give 0.464 g (90%) of 2-aminoethyl 6-O-t-butyldimethylsilyl-2-deoxy-2-amino)-β-D-glucopyranoside as a white solid (compound 18a; X=O, n9)=p=q=0, $R_4$=$R_5$=$R_6$=$R_7$=H, $PG_2$=TBDMS).

Example 7

Alternate preparation of 2-aminoethyl 6-O-t-butyldimethylsilyl-2-deoxy-2-amino)-β-D-glucopyranoside (compound 18a; X=O, n=m=p=q=0, $R_4$=$R_5$=$R_6$=$R_7$=H, $PG_2$=TBDMS), Namely

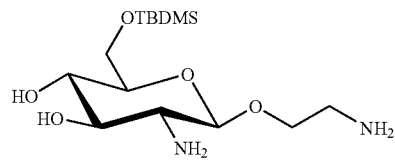

using phthalimide protection. This example utilizes a process as shown in Scheme 2.

(1) A mixture of 2-deoxy-2-phthalimido-1,3,4,6-tetra-O-acetyl-α,β-D-glucopyranose (compound 15, PG=Phth, Z=Oac; 0.20 g, 0.42 mmol), N-(2-hydroxyethyl)phthalimide 0.26 g, 0.84 mmol), and 4 A molecular sieves (0.15 g) in anhydrous $CH_2Cl_2$ (2.5 mL) under nitrogen was stirred for 20 min at room temperature and then treated dropwise with $SnCl_4$ (1.0 M in $CH_2Cl_2$; 0.8 mL, 0.8 mmol). The resulting pink slurry was stirred for 72 h at room temperature, partitioned between ice cold saturated aq. $NaHCO_3$ and $CHCl_3$, and filtered through celite. The layers were separated and the organic layer was washed with water, dried ($Na_2SO_4$) and concentrated. Flash chromatography on silica gel eluting with EtOAc-hexanes afforded 0.19 gm (75%) of 2-(phthalimido)ethyl 3,4,6-tri-O-acetyl-2-deoxy-2-phthalamido-β-D-glucopyranoside as an amorphous solid (compound 17; X=O, n=m=p=q=0, $R_4$=$R_5$=$R_6$=$R_7$=H, PG=Phth).

(2) A solution of the compound prepared in (1) above (0.712 g, 1.17 mmol) in methanol (40 mL) was treated with a solution of 25% sodium methoxide in methanol (0.15 mL) and stirred for 20 min at room temperature. The reaction mixture was neutralized with Amberlite IT-120 (H+) resin (0.5 g), filtered, concentrated, and dried at high vacuum overnight to give 0.56 g (~100%) of 2-(phthalimido)ethyl 2-deoxy-2-(benzyloxycarbonylamino)-β-D-glucopyranoside as a white solid (compound 17a; X=O, n=m=p=q=0, $R_4$=$R_5$=$R_6$=$R_7$=H, PG=Phth), which was used without further purification in the next step.

(3) A solution of the compound prepared in (2) above (0.55 g, 1.14 mmol) in anhydrous pyridine (9.5 mL) at room temperature was treated with TBDMS-CI (1.1 equiv) and stirred at room temperature for 2 h. Additional TBDMS-CI (1.6 equiv) was added in two portions over 2 h and the resulting mixture was stirred another 2 h at room temperature. The reaction mixture was diluted with water and extracted with EtOAc. The layers were separated and the organic phase was washed with brine, dried ($Na_2SO_4$), and concentrated. Flash chromatography with $CHCl_3$-MeOH afforded 0.67 g (96%) of 2-(phthalimido)ethyl 6-O-t-butyldimethylsilyl-2-deoxy-2-(phthalimido)-β-D-glucopyranoside compound as a white solid (compound 18; X=O, nm-=p=q=0, $R_4$=$R_5$=$R_6$=$R_7$=H, PG=Phth, $PG_2$=TBDMS).

(4) A mixture of the compound prepared in (3) above (0.65 g, 1.09 mmol) in n-butanol (11 mL), 4 A molecular sieves (0.5 g), and polystyrene-bound ethylene diamine (1% cross-linked, 50-100 mesh, 7.5 g) was heated to reflux overnight. The reaction mixture was filtered and concentrated. The residue obtained was lyophilized from dioxane to give 0.37 g (~100%) of 2-aminoethyl 6-O-t-butyldimethylsilyl-2-deoxy-2-amino)-β-D-glucopyranoside as a white solid (compound 18a; X=O, n=m=p=q=0, $R_4=R_5=R_6=R_7$=H, $PG_2$=TBDMS All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for preparing an aminoalkyl glucosaminide 4-phosphate compound having the formula:

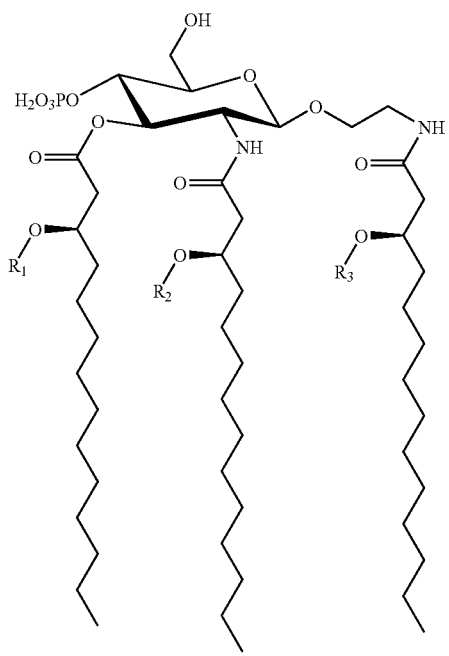

wherein $R^1$, $R^2$, and $R^3$ are each independently selected from saturated and unsaturated ($C_2$-$C_{24}$) aliphatic acyl groups;

comprising (a) reacting a compound having the formula

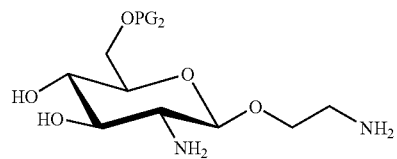

wherein $PG_2$ represents a hydroxyl protecting group, with a carboxylic acid having the formula $CH_3(CH_2)_{10}CH(OR^1)CH_2COOH$ if $R^1$, $R^2$ and $R^3$ are identical acyl groups or sequentially with carboxylic acids having the formula $CH_3(CH_2)_{10}CH(OR^1)CH_2COOH$, $CH_3(CH_2)_{10}CH(OR^2)CH_2COOH$ and $CH_3(CH_2)_{10}CH(OR^3)CH_2COOH$ if $R^1$, $R^2$ and $R^3$ represent two or three different acyl groups;

(b) phosphorylating the 4-hydroxyl group thereby introducing a phosphate protecting group onto the 4-hydroxyl position;

and (c) removing the protecting group $PG_2$ and the phosphate protecting group.

2. A method according to claim 1 wherein the phosphate protecting group is benzyl or substituted benzyl.

3. A method according to claim 1 wherein the phosphate protecting group is t-butyl.

4. A method according to claim 1 wherein the phosphate protecting group is 2,2,2-trichloroethyl.

5. A method according to claim 1 wherein the phosphate protecting group is 2-trimethylsilylethyl.

6. A method according to claim 1 wherein the phosphate protecting group is allyl.

7. A method according to claim 1 wherein $R^1$, $R^2$ and $R^3$ are identical acyl groups.

8. A method according to claim 1 wherein $R^1$, $R^2$ and $R^3$ represent two or three different acyl groups.

* * * * *